United States Patent
Nelles et al.

(10) Patent No.: US 6,700,058 B2
(45) Date of Patent: Mar. 2, 2004

(54) HOLE TRANSPORTING AGENTS AND PHOTOELECTRIC CONVERSION DEVICE COMPRISING THE SAME

(75) Inventors: Gabriele Nelles, Stuttgart (DE); Akio Yasuda, Stuttgart (DE); Hans-Werner Schmidt, Bayreuth (DE); Thelakkat Mukundan, Bayreuth (DE); Haridas R. Karickal, Bayreuth (DE); Donal Lupo, Dublin (IE)

(73) Assignee: Sony International (Europe) GmbH, Berlin (DE)

( * ) Notice: Subject to any disclaimer, the term of this patent is extended or adjusted under 35 U.S.C. 154(b) by 0 days.

(21) Appl. No.: 09/866,199

(22) Filed: May 25, 2001

(65) Prior Publication Data

US 2002/0036298 A1 Mar. 28, 2002

(30) Foreign Application Priority Data

May 29, 2000 (EP) ............................. 00111493

(51) Int. Cl.$^7$ ..................... H01L 51/20; C07C 211/54
(52) U.S. Cl. ..................... 136/263; 136/258; 136/256; 257/43; 257/40; 257/53; 257/431; 438/85; 438/96; 438/82; 564/434; 429/111
(58) Field of Search ............................. 136/263, 258, 136/256; 257/43, 40, 53, 431; 438/85, 96, 82; 429/111; 564/434

(56) References Cited

U.S. PATENT DOCUMENTS

| | | | |
|---|---|---|---|
| 5,885,368 A | * 3/1999 | Lupo et al. ............. | 136/263 |
| 6,291,763 B1 | * 9/2001 | Nakamura ............ | 136/256 |
| 6,335,480 B1 | * 1/2002 | Bach et al. ............ | 136/263 |
| 6,350,946 B1 | * 2/2002 | Miyake et al. ......... | 136/252 |
| 6,376,765 B1 | * 4/2002 | Wariishi et al. ........ | 136/263 |
| 6,495,067 B1 | * 12/2002 | Ono ..................... | 252/299.61 |

FOREIGN PATENT DOCUMENTS

| | | |
|---|---|---|
| EP | 0 611 148 | 8/1994 |
| EP | 0 901 175 | 3/1999 |
| EP | 901175 A2 | * 3/1999 |
| WO | WO 98/48433 A1 | * 10/1998 |

OTHER PUBLICATIONS

Hagen et al, "Novel hybrid solar cells consisting of inorganic nanoparticles and an organic hole transport material," Synthetic Metals, vol. 89, (1997), pp. 215–220.*

Bach et al, "Solid–state dye–sensitized mesoporous TiO2 solar cells with high photon–to–electron conversion efficiencies," Nature, vol. 395, Oct. 8, 1998, pp. 583–585.*

Hagen et al: "Novel Hybrid Solar Cells Consisting of Inorganic Nanoparticles and an Organic Hole Transport Material" Synthetic Metals, CH, Lausanne, vol. 89, Sep. 1997, pp. 215–220, XP002108277.

Bach U et al: "Solid–State Dye–Sensitized Mesoporous TIO2 Solar Cells with High Photon–To–Electron Conversion Efficiencies" Nature, GB, Macmillan Journals LTD. London, vol. 395, Oct. 8, 1998, pp. 583–585, XP000783901.

Thelakkat M et al: "Synthesis and Properties of Novel Hole Transport Materials for Electroluminescent Devices" Macromolecular Symposia, DE, Wiley VCH, Weinheim, vol. 125, 1998, pp. 157–164, XP000738958.

Thelakkat M et al: "Synthesis and Properties of Novel Derivatives of 1, 3, 5–Tris (Diarylamino) Benzenes for Electroluminescent Devices" Advanced Materials, VCH Verlagsgesellschaft, Weinheim, DE, vol. 10, No. 3, Feb. 11, 1998, pp. 219–223, XP000732696.

* cited by examiner

*Primary Examiner*—Alan Diamond
(74) *Attorney, Agent, or Firm*—Frommer Lawrence & Haug LLP; William S. Frommer; Samuel H. Megerditchian

(57) ABSTRACT

A photoelectric conversion device comprising a semiconductor and an organic electrically conducting agent, wherein the organic electrically conducting agent exhibits a melting temperature $T_m$ which is lower than the operation temperature of the photoelectric conversion device.

19 Claims, 11 Drawing Sheets a)

b)

Figure 1:
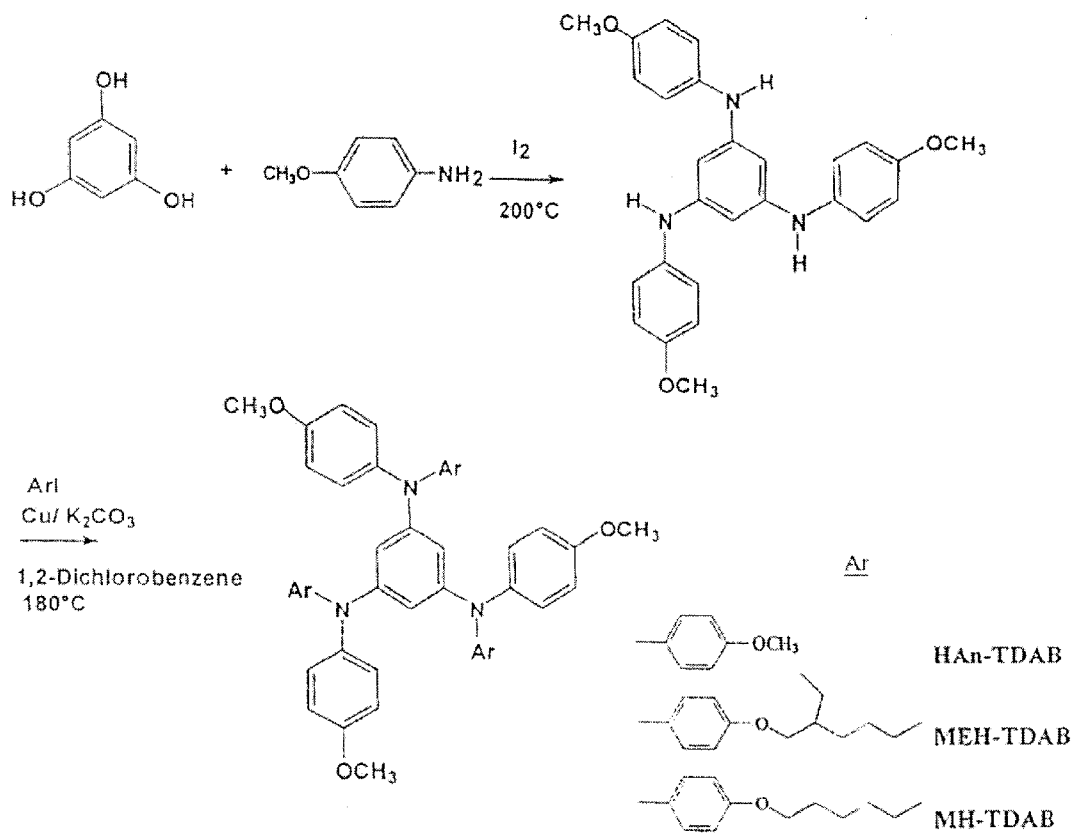

| Compound Ar | $T_g$ [°C] | $T_{cr}$ [°C] | HOMO [eV] |
|---|---|---|---|
| —⟨⟩—OCH₃ | - | 130 | -4.98 |
| —⟨⟩—O—⟨⟩ | 54 | - | -5.07 |
| —⟨⟩—⟨⟩ | 85 | 135 | -5.11 |
| naphthyl | 88 | - | -5.13 |
| anthryl | 123 | - | -5.07 |

HOLE TRANSPORTING AGENTS AND PHOTOELECTRIC CONVERSION DEVICE COMPRISING THE SAME

The present invention is related to a photoelectric device, hole transporting agents, uses and mixtures thereof, solar cells comprising the same and methods for the manufacture of photoelectric conversion devices.

Since the demonstration of crystalline silicon p/n junction solar cell in 1954 by Chapin et al. with a reported efficiency of 6%, there was a dramatic increase in the efficencies of such cells as a result of improvements in current, significant increase in voltage and splitting the sunlight among solar cells of differing band gaps. The higher voltages resulted directly from increasing the densities of minority carriers generated by absorbed sunlight. By reducing the minority carrier recombination rate, trapping light in active layers and by increasing the intensity of light with concentration optics, efficiencies as high as 25–30% have been reported for two band-gap single crystal laboratory cells like AlGaAs/GaAs. Thin film multijunction, multiband-gap cells using hydrogenated amorphous silicon (a-Si:H) or polycrystalline alloys exhibit up to 15% laboratory efficiency. The efficiencies of commercial power systems in the field remain in the range of 3 to 12%.

As an alternative a dye sensitized semiconductor-electrolyte solar cell was developed by Grätzel et al. consisting of titanium dioxide nanoparticles with a ruthenium complex adsorbed on the surface an iodine-iodide electrolyte as disclosed in WO 91/16719. The ruthenium complex acts a as sensitizer, which absorbs light and injects an electron into titanium dioxide; the dye is then regenerated by electron transfer from the iodine-iodide redox couple. The advantage of such a solar cell results from the fact that no crystalline semiconductors have to be used anymore while already providing conversion efficiencies of light into electrical energy of up to 12% (O'Regan, B. et al; Nature (1991), 353, p. 737).

The iodine-iodide redox system imposes several limitations to the dye sensitized semiconductor-electrolyte solar cell such as offensiveness of these compounds and limitations in adapting the system's energy levels to the one of the dye. WO 98/48433 discloses the use of a hole transporting material as the redox system in such a solar cell. The hole transporting materials disclosed are spiro fluorene compounds which are dissolved in some electrolytic solution. The same type of compounds for use as hole transporting material is disclosed in Bach et al. (Bach et al.; Nature (1998), 395, p.583–585).

EP 0 901 175 A2 discloses the use of other organic hole transporting materials such as aromatic tertiary amine compounds. The application of the organic hole transporting material can be performed by vacuum evaporation or by coating using a coating solution. The selection of the solvent used for the preparation of the coating solution focuses on a combination of low viscosity and low vapor pressure which requires a compromise. Additionally, the solvent has to exhibit a distinct anodic boundary potential.

The problem underlying the present invention is to provide for a photoelectric conversion device comprising a nanoparticulate semiconductor which may be sensitized with a dye, and an organic hole transporting agent whereby the organic hole material is in intimate contact with the semiconductor or—if present—with the dye. In another aspect the underlying problem is related to a photoelectric conversion device comprising a nanoparticulate semiconductor which may be sensitized with a dye, and an organic hole transporting agent which exhibits a higher photo-to-electron conversion efficiency and light-to-electric energy conversion efficiency than the respective devices known in the prior art.

A further object of the present invention is to provide compounds which can be used as hole transporting materials in photoelectric conversion devices.

A still further objective of the present invention is to provide a method for the manufacture of a photoelectric device, more particularly of photoelectric device exhibiting the favorable characteristics as defined above.

This problem is solved in a first aspect by a photoelectric conversion device comprising a semiconductor and an organic electrically conducting agent, wherein said organic electrically conducting agent exhibits a melting temperature Tm which is lower than the operation temperature of the photoelectric conversion device.

This problem is solved in a second aspect by a photoelectric conversion device comprising a semiconductor and an organic electrically conducting agent, wherein the melting temperature Tm of the organic electrically electrically conducting agent is about 140° C. or less.

This problem is furthermore solved in a third aspect by a photoelectric conversion device comprising a semiconductor and an organic electrically conducting agent, wherein the organic electrically conducting agent is present in a solid but non-crystalline form.

This problem is finally solved in a fourth aspect by a photoelectric conversion device comprising a semiconductor and an organic electrically conducting agent, wherein said organic electrically conducting agent exhibits a glass-transition temperature $T_g$ of about 60° C. or less.

In a preferred embodiment of the inventive photoelectric conversion device wherein the organic electrically conducting agent is present in a solid but non-crystalline form; the organic electrically conducting agent is present in an amorphous form. In an alternative embodiment, the glass transition temperature Tg of the organic electrically conducting agent is at or below the operation temperature range of the photoelectric device.

In a preferred embodiment of the inventive device according to any of the various above aspects the electrically conducting agent exhibits a glass-transition temperature $T_g$ of about 60° C. or less.

In a preferred embodiment of the photoelectric devices according to any of the aspects described above said organic electrically conducting agent exhibits a glass-transition temperature $T_g$ of about 40° C. or less, preferably of about 30° C. or less and more preferably of about 20° C. or less.

In an even more preferred embodiment of the inventive photoelectric devices said organic electrically conducting agent exhibits a glass-transition temperature $T_g$ of about 10° C. or less and preferably of about 0° C. or less.

In a further embodiment of the photoelectric devices according to above aspects said organic electrically conducting agent comprises at least one organic compound.

In another preferred embodiment of the photoelectric device the semiconductor is sensitized with a dye.

In a preferred embodiment of the inventive photoelectric devices said organic electrically conducting agent comprises a mixture of at least two organic compounds.

In another embodiment of the inventive photoelectric devices said organic electrically conducting agent further comprises at least one dopant.

In an embodiment of the inventive photoelectric devices said organic electrically conducting agent is a hole transporting agent.

In a further embodiment the inventive photoelectric devices said dye is a ruthenium complex.

In still a further embodiment of the inventive photoelectric devices said semiconductor is porous.

In a preferred embodiment said semiconductor comprises nanoparticles, preferably nanoparticles of $TiO_2$.

The problem is also solved by a compound acting as a hole transporting agent which is a triphenyldiamine derivative represented by formula (I)

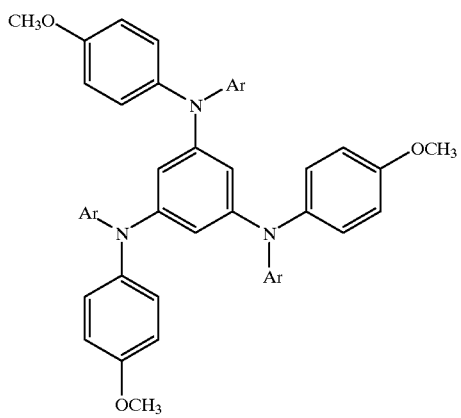

(I)

wherein Ar is a substituent represented by formula (II)

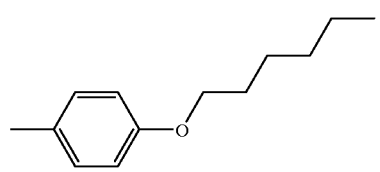

(II)

The problem is also solved by a compound acting as a hole transporting agent which is a triphenyldiamine derivative represented by formula (III)

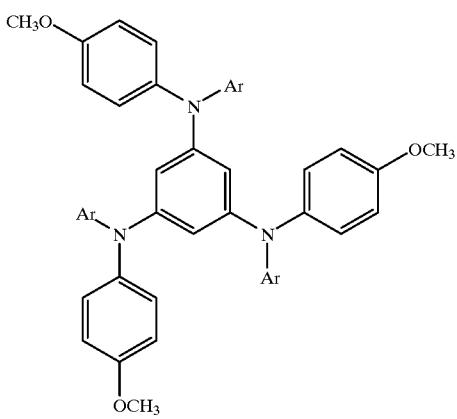

(III)

wherein Ar is a substituent represented by formula (IV)

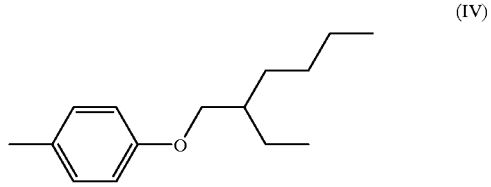

(IV)

In a further aspect the problem is solved by the use of the inventive compounds, i.e. the compound as represented by formulae (I) and (II) or a compound as represented by formulae (III) and (IV) in the inventive devices, more particularly as the organic electrically conducting agent.

In still a further aspect the problem is solved by a mixture comprising the inventive compounds, i.e. the compound as represented by formulae (I) and (II) and the compound as represented by formulae (III) and (IV).

In a preferred embodiment of the inventive mixture the ratio in said mixture of the compound according to formulae (I) and (II), i.e. MH-TDAB, in relation to the compound according to formulae (III) and (IV), i.e. MEH-TDAB, is from about 60:40 to a about 20:80, preferably 40:60, wherein the amount of each compound is expressed as wt.-% of the total weight of the mixture.

In a further aspect the problem is solved by the use of the inventive mixture in any of the inventive devices, particularly as an electrically conducting agent.

In a still further aspect the problem is solved by the use of the inventive mixture for the manufacture of any of the inventive devices, particularly as an electrically conducting agent.

The problem is also solved by a method for the production of a photoelectric conversion device, preferably any of the inventive photoelectric devices, comprising the step of applying any of the inventive compounds or any of the inventive mixtures to a semiconductor sensitized with a dye.

In an embodiment the inventive method the application step is carried out at a temperature at or above the glass-transition temperature of the electrically conducting agent.

In a further embodiment of the inventive method the method further comprises at least one of the following steps:
 providing a semiconductor,
 melting the organic electrically conducting agent,
 applying said organic electrically agent to said semiconductor sensitized with a dye, and
 connecting electrodes to said semiconductor and to said organic electrically conducting agent.

In another embodiment the semiconductor is sensitized with a dye.

In a still further embodiment of the inventive method said organic electrically conducting agent is applied to said semiconductor such that a layer of said agent persists on top of said semiconductor.

In another embodiment of the inventive method said method comprises the step of cooling the semiconductor and said organic electrically conducting agent to a temperature below said melting temperature and above the glass transition temperature of said organic electrically conducting agent.

In a further aspect the problem is solved by a solar cell comprising the inventive photoelectric conversion device.

There are several surprising findings underlying the present invention.

Basically, the invention is based on the finding that a critical aspect of the manufacture of photoelectric conversion devices comprising a semiconductor and which are preferably based on dye-sensitized colloidal $TiO_2$ comprising an organic hole conductor, i.e. organic solid state solar cells, is the pore filling of the organic electrically conducting agent. However, the pore filling is also regarded as a crucial factor for establishing high performance solar cells of that type. To prepare the hole transport layer, usually the material will be dissolved in a suitable solvent and spin coated or pipetted. Thereby the solvent evaporates. Besides the limitations known from the prior art in relation to the preparation of a suitable solution, additionally, the use of such solution is critical for the following two reasons. First, the hole transporting agent containing solution has to go into the pores. Second, the hole transporting material should stay in close contact with the surface even after the solvent evaporates. In practice, however, the solution does not go easily into the pores and the hole transporting material shrinks and dewets after the drying. The same considerations generally apply to any electrically conducting agents.

In view of this, the inventors have found that the selection of the organic electrically conducting agent or material is important and should follow some guidelines which define the appropriate organic electrically conducting agents. The basis of this is the idea to have said organic electrically conducting agent in a non-crystalline form layered on the semiconductor which may optionally be dye sensitized as the crystalline form prevents the required intimate contact between the semiconductor and the organic electrically conducting agent and the semiconductor or the dye, respectively. On the other hands systems are disadvantageous where the electrically conducting agent is present in a solution, i.e., in the form of an aqueous electrolyte. To avoid the disadvantages of any of these conventional systems, the inventors provide basically the following strategies for the organic electrically conducting agent: The electrically conducting agent may be in a liquid or viscous form thus providing the desired intimate contact between said agent and the semiconductor or the dye in the process of manufacturing and/or during operation of the photoelectric conversion device. (In the latter case, it is preferred when the organic electrically conducting agent is amorphous.) Or the organic electrically conducting agent may be in the solid form, preferably also in the operation mode, however, again in a non-crystalline form. This can be reached by the material being amorphous or by the electrically conducting material having a glass-transition temperature $T_g$ at or below the operation temperature of the photoelectric conversion device.

Based on this, the following guidelines for selecting appropriate organic electrically conducting agents were formulated which concomitantly define the features of the organic electrically conducting agents used according to and in the present invention.

First, the organic electrically conducting agents exhibit a melting temperature which is lower than the operation temperature of the photoelectric devise.

Second, the melting point of the organic electrically conducting agents is about 140° C. or less.

Third, the organic electrically conducting agents are present in the photoelectric device in a solid state but in a non-crystalline form. This can either or in parallel be realized if the organic electrically conducting agent as such is amorphous, preferably under the operation conditions and/or the manufacturing conditions, or if the glass transition temperature $T_g$ of the organic electrically conducting agent is at or below the operation temperature range of the photoelectric device.

Fourth, the organic electrically conducting agents exhibit a glass transition temperature Tg of about 60° C. or less.

Fifth, the organic electrically agents exhibit a coefficient of viscosity, expressed as poise (1/(ml s)), between 10 and 200, preferably between 10 and 150, more preferably between 10 and 100 and even more preferable 10 and 50. The above values were determined using a viscosimeter which is based on the capillary measurement technique. The viscosity should be rather low, particularly during the manufacturing process to allow for the intended intimate contact. The viscosity, however, may also be low during operation of the photoelectric device comprising such organic electrically conducting material, particularly in case said material is not amorphous. Additionally, even if the viscosity should be rather, low while manufacturing the cells, during operation it should not be as low as an electrolyte to avoid the sealing problems observed with the liquid (solar) cells.

It is clear that the above criteria may specify different compounds or mixtures of compounds used as the organic electrically conducting agent according to or in the meaning of the present invention. It is also clear that some appropriate organic electrically conducting materials or agents will meet more than one of the above criteria. It is, however, not necessary that an organic electrically conducting agent or a respective mixture thereof meets all of the above criteria although this may be possible.

It is also within the scope of the present invention that the operation temperature range may have an impact with regard to the selection criteria for suitable organic electrically conducting material. Typically, the glass transition temperature Tg of the organic electrically conducting agent(s) is lower than the operation temperature. In a further scenario both the melting temperature Tm as well as the glass transition temperature is lower than the operation temperature (range). Further electrically conducting material useful in the meaning of the present invention are those with low Tg and higher Tm in relation to the operation temperature or operation temperature range, with a Tm far below the operation temperature, both low Tg and Tm around operation temperature, and material without a Tg, i.e. amorphous material.

It is to be noted that the organic electrically conducting agent may be a semiconductor.

By choosing the organic electrically conducting agents along the guidelines disclosed herein, the inventors could overcome the difficulties associated with the hole conductor materials of the prior art. The reason for this is that due to these material characteristics there is no crystallization of the organic electrically conducting material once said material is applied to the semiconductor and thus no dewetting. Consequently, the organic electrically conducting material stays in intimate contact with the semiconductor (which may preferably be dye-sensitized in that case intimate contact with the dye is meant) which provides for a high performance. In general terms, suitable organic electrically conducting materials are beyond those defined above also those which have a high amorphous character, a low Tg and melting points around or lower than room temperature.

Some materials meeting these requirements are compounds, particularly hole transporting agents, which are derived from similar compounds known in the art and comprise linear as well as branched or starburst structures and polymers carrying long alkoxy groups as side-chains or in the backbone. Such hole transporting agents are in principle disclosed in EP 0 901 175 A2, the disclosure of which is incorporated herein by reference.

The derivatization of such compounds by branched or starburst structures and more particularly if these structures comprise suitable soft alkoxy chains, confers the desired characteristics to the organic electrically conducting agent, i.e. a decrease in viscosity and an increase in the capillary effect.

Other possible organic electrically conducting agents are, e.g., described in WO 98/48433, EP 0 901 175, DE 19704031.4 and DE 19735270.7. The latter two references disclose TDAB for application in OLEDs (i.e. organic light emitting diodes). It is to be noted that any of the known TDAB may be—further—derivatized such as by using substitutions such as alkoxy, alkyl, silyl at the end-standing phenyl rings which could be in p-, m- and o-position mono-, bi-, or tri-substituted.

More particularly, WO 98/48433 the disclosure of which is incorporated herein by reference, discloses as organic hole transporting agent triphenyl methane, carbazole and TPD (N,N'-diphenyl-N,N'-bis(3-methylphenly)-(1,1'-bi'phenyl)-4,4'-diamine. Said hole transporting agents may be spiro or heterospiro compounds as of formula (1)

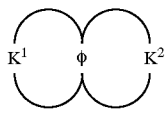

(1)

wherein φ means C, Si, Ge or Sn, preferable C, Si or Ge and more preferably C or Si ad most preferably C and K1 and K2 are independent from each other conjugated systems.

Spiro compounds are compounds wherein two ring systems are linked to each other by a tetracovalent atom. This atom is referred to as spiro atom as defined in the Handbook of Chemistry and Physics $62^{nd}$ ed. (1981-2), CRC Press, p. C-23 to C-25. The term spiro compoud shall mean monomeric and polymeric carbospiro and heterospiro compounds.

Preferred compounds according to formula (1) are 9,9'spirobifluorene derivateives according to formula (2).

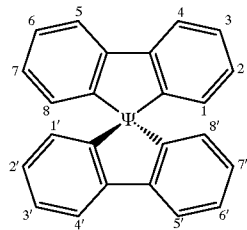

(2)

wherein φ has the same meaning as specified above and the benzo groups may be independently substituted and/or anellated.

Particularly preferred are the spirobifluorene derivateive according to formula (3)

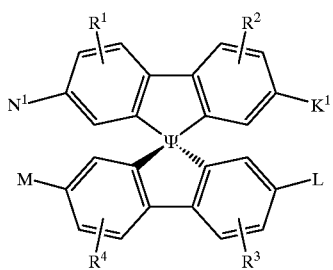

(3)

Wherein the symbols and indices have the following meanings

φ is C, Si, Ge, or Sn, preferably C, Si, Ge and more preferably C, Si and most preferred C, K1, L, M, N1, R1, R2, R3, R4 are identical or different and represent:

a) hydrogen, $NO_2$—, —CN, —F or Cl, b) a linear or branched alkyl residue of 1 to 20 C atoms, wherein, b1) one or more non-juxtaposed CH2-groups may be replaced by —O—, —S—, —CO—O—, —O—CO—, —O—CO—O—, NR5 or —Si(CH3)2 and/or b2) one or more CH2 groups may be replaced by —CH=CH—, —C≡C—, 1,4-phenylene, 1,4-cyclohexylene (cyclohexamethylene) or 1,3-cyclopentylene (cyclopentamethylene) and/or b3) one or more H atoms may be replaced by F and/or Cl and/or c) one of the following groups

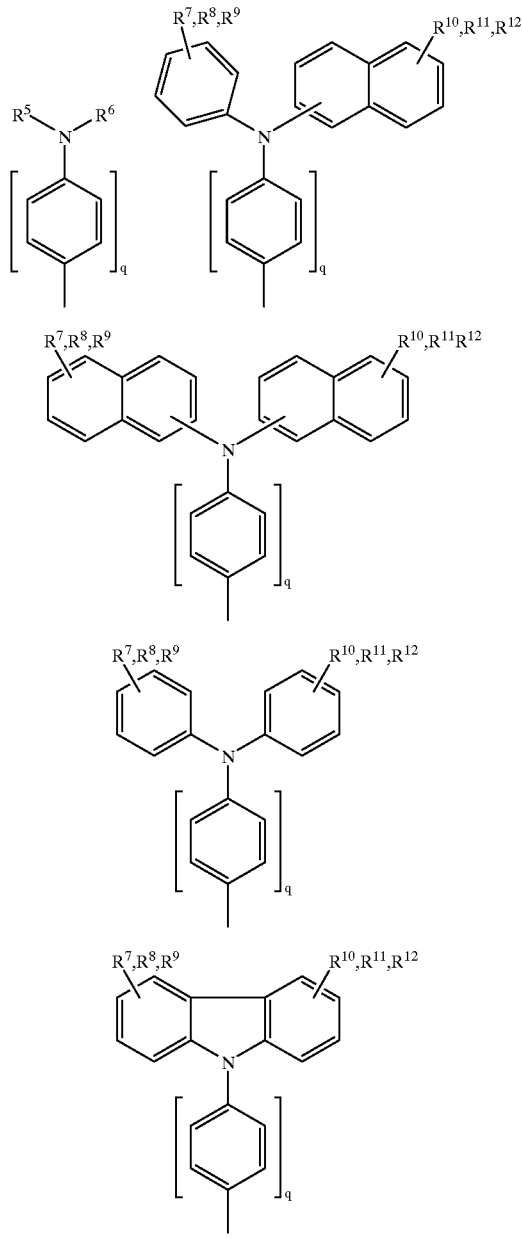

-continued
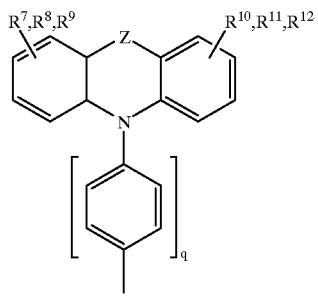
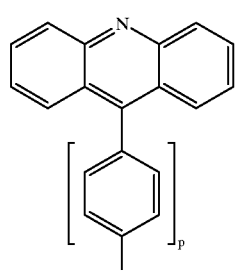
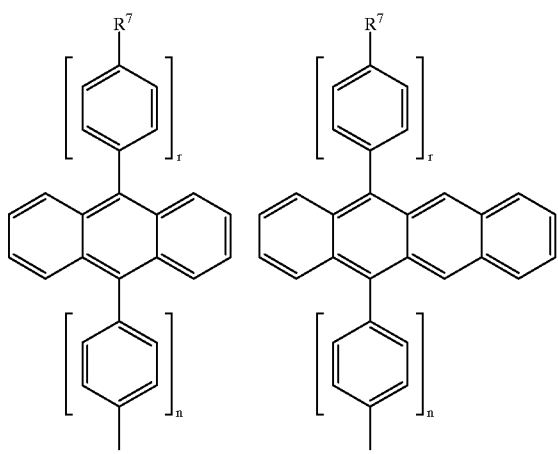
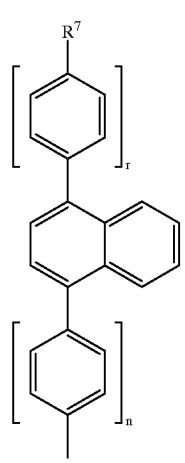
-continued
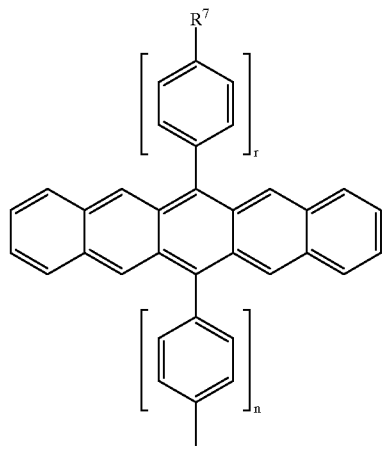
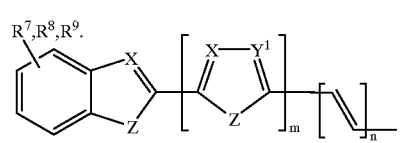
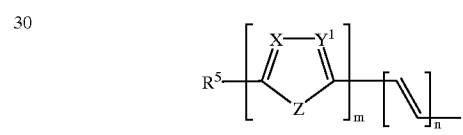
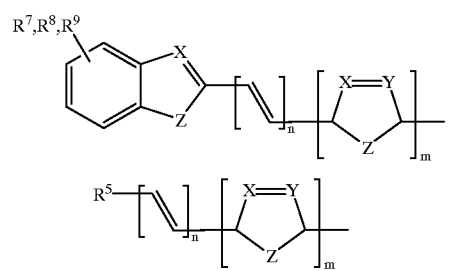
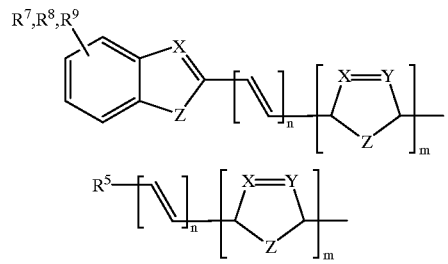
X, Y1 are each identical or different =CR7- or =N—;
Z is —O—, —S—, NR5-, —CRR—, —CR=CR— or —CR=N—;
R5, R6 are each identical or different
  a) hydrogen
  b) a linear or branched alkyl residue of 1 to 20 C atoms wherein
    b1) one or more CH2 groups which are non-juxtaposed and which are not bound to nitrogen may be replaced by —O—, —S—, —CO—O—, —O—CO—, —O—CO—O— or —Si(CH3)2 and/or b2) one or more CH2 groups may be replaced by —CH=CH—, —C≡C—, cyclopropane-1,2-diyl, 1,4-phenylene, 1,4-cyclohexylene or 1,3-cyclopentylene and/or b3) one or more H atoms may be replaced by F and/or Cl and/or b4) R5 and R6 may form a ring;

c) phenyl, biphenyl, 1-naphthyl, 2-thienyl, 2-furanyl;

R7, R8, R9, R10, R11, R12 are identical or different a) hydrogen, —CN, —F, NO2 or —Cl b) a linear or branched alkyl residue with 1 to 20 C atoms, wherein b1) one or more of the non-juxtaposed CH2 groups may be replaced by —O—, —S—, —CO—O—, —O—CO—, —O—CO—O—, —NR5 or —Si(CH3)2- and/or b2) one or more CH2 groups may be replaced by —CH=C—, —C≡C—, cyclopropane-1,2-duiyl, 1,4-phenylene, 1,4-cyclohexylene or 1,3 cyclopentylene and/or b3) one or more H atoms may be replaced by F and/or Cl;

m,n,p,q,r are either identically or differently 0, 1, 2, 3, 4, 5 or 6, preferably 0, 1, 2 ,3 ,4, 5 or 6, preferably 0, 1, 2, 3, 4, more preferably 0, 1, 2 or 3.

Particularly preferred are the spirobifluorene derivatives according to formulae (4) a–c

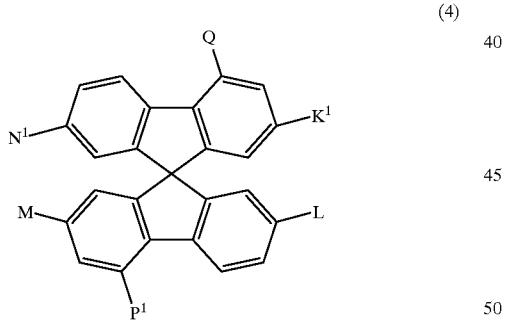

(4)

Wherein the symbols have the following meanings:

4.a) K1=L=M=N1=

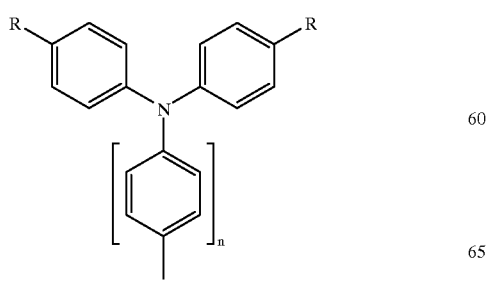

-continued

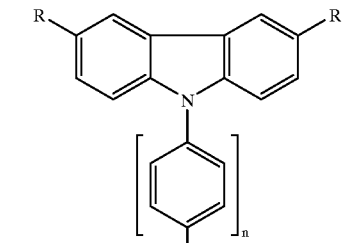

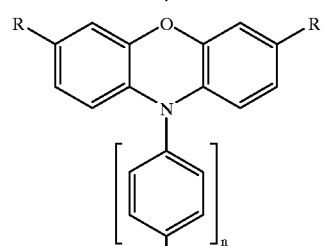

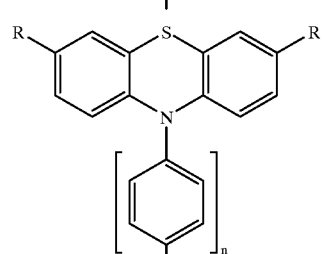

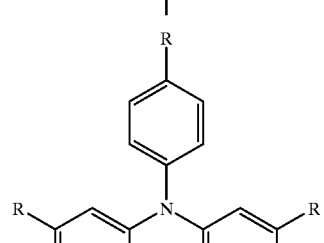

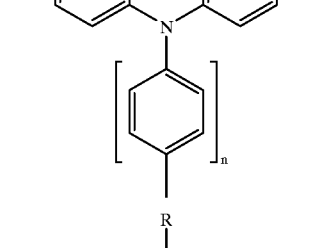

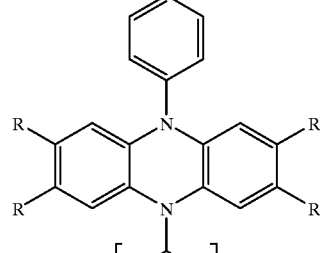

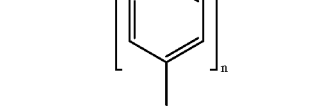

-continued

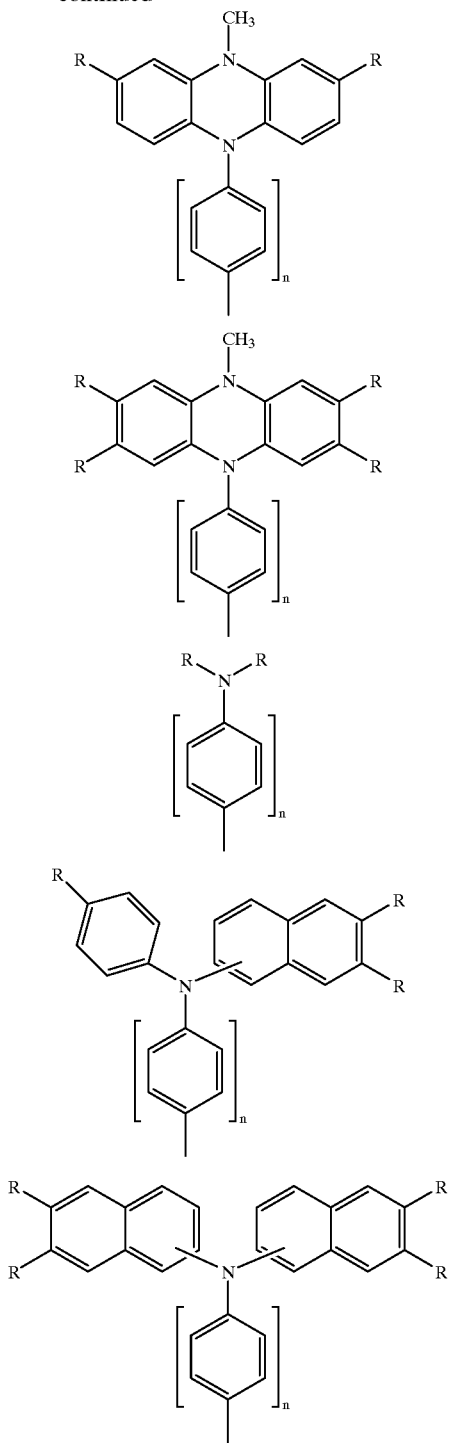

R is identically or differently H, alkyl, —O-alkyl-, —S-alkyl- with each 1 to 20 C atoms, preferably 1 to 4 C atoms, panly, biphenyl, 1-naphthyl, 2-naphthyl, 2-thienyl, 2-furanyl, —O-phenyl, —O-Biphenyl, —O-1-naphthyl, —O-2-naphthyl, —O-2-thienyl, —O-2-furanyl, —CN—NR$_2^+$, whereinO-alkyl/aryl, S-alkyl/aryl, CN and NR2 must not be linked to nitrogen;

n=1, 1, 2, 3, 4.

and Q, P$^1$ are identical or different and selected from the group comprising

H, COOR, CH$_2$OR,

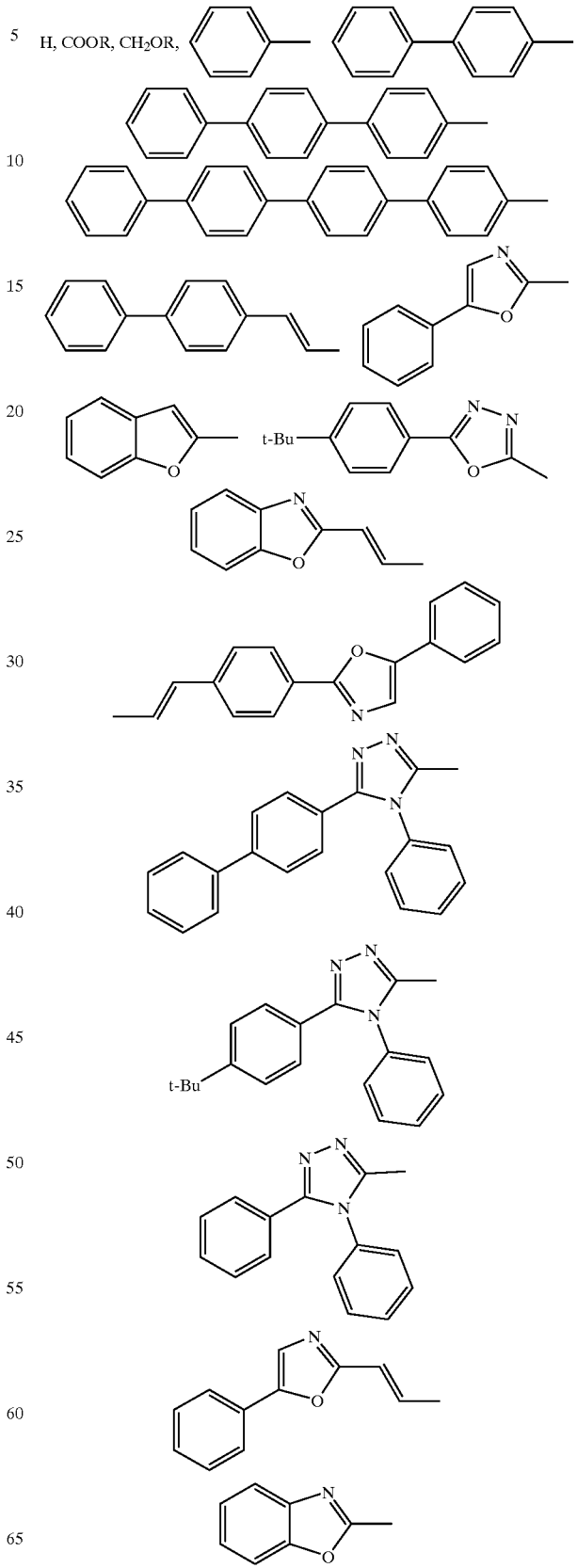

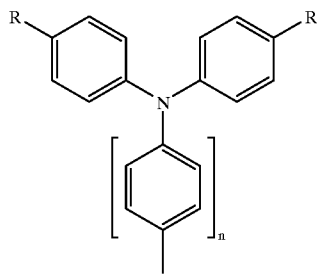
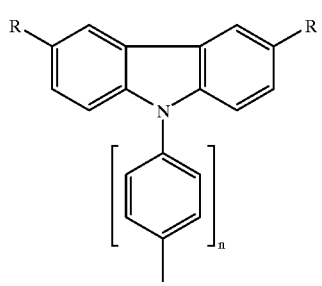
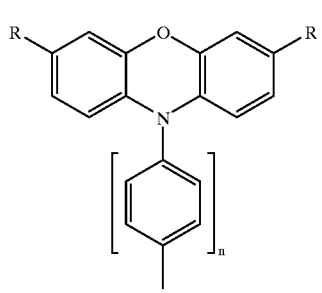
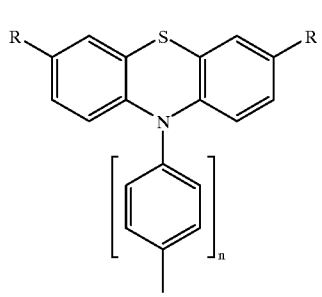
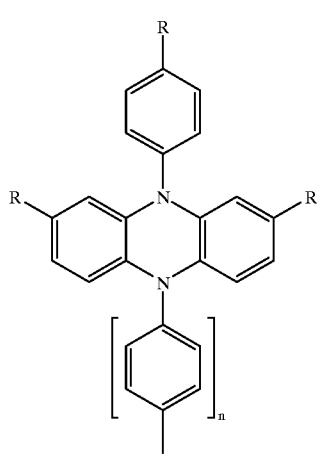
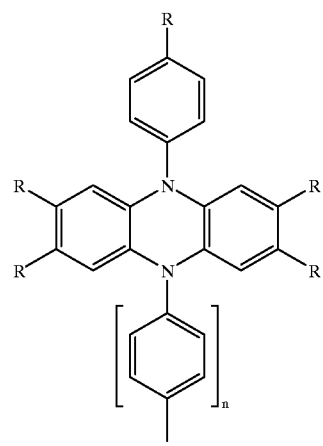
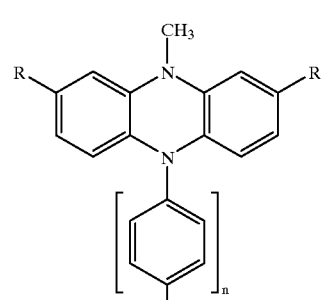
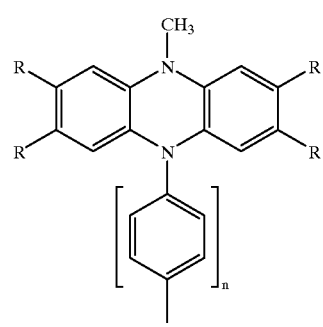
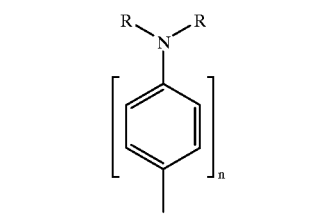
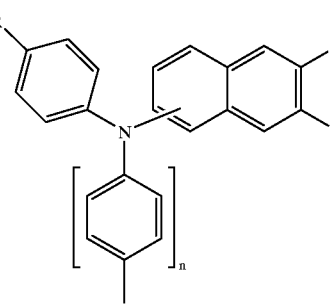

-continued
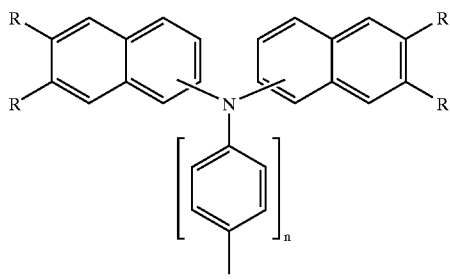
wherein the above symbols and indices have the meanings as specified above.
4.b) $K^1=N^1$ and is selected from the group
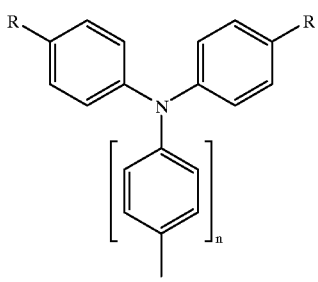
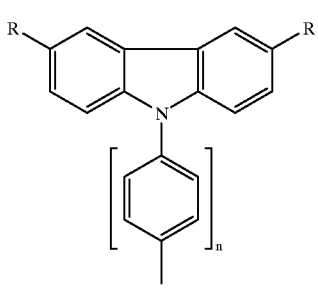
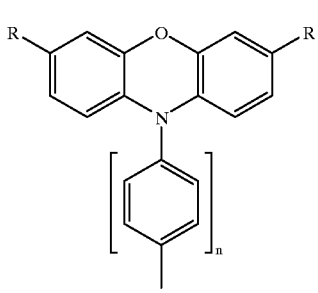
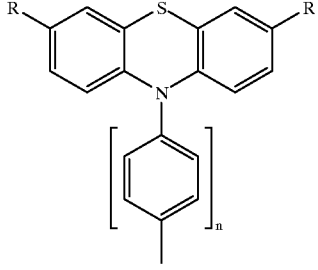
-continued
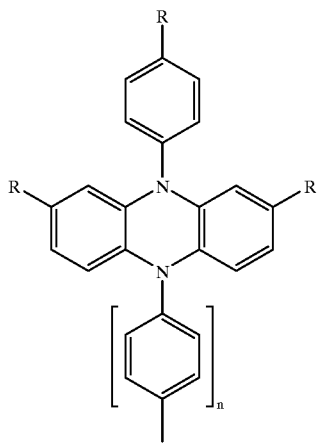
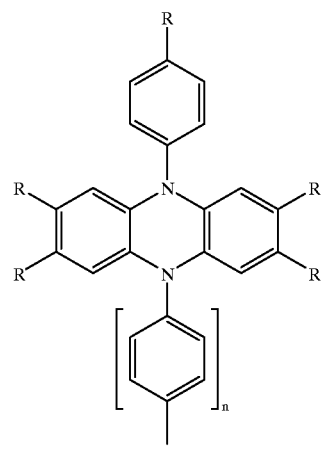
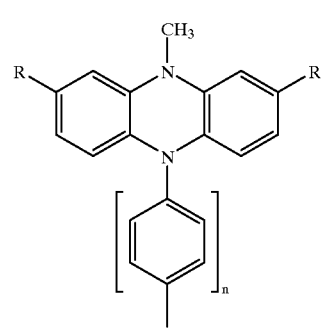
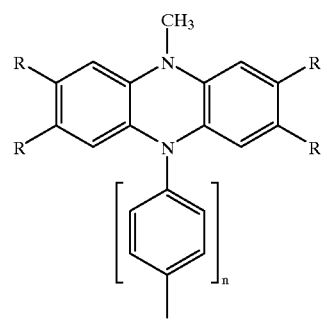

-continued
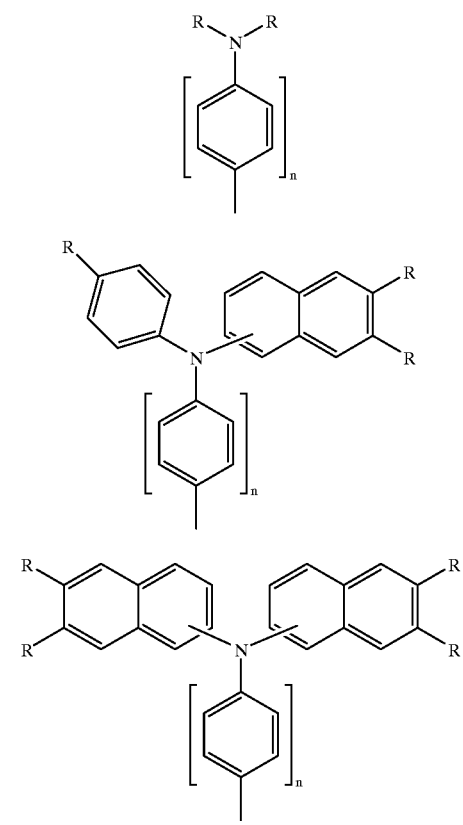
and L=M and is selected from the group
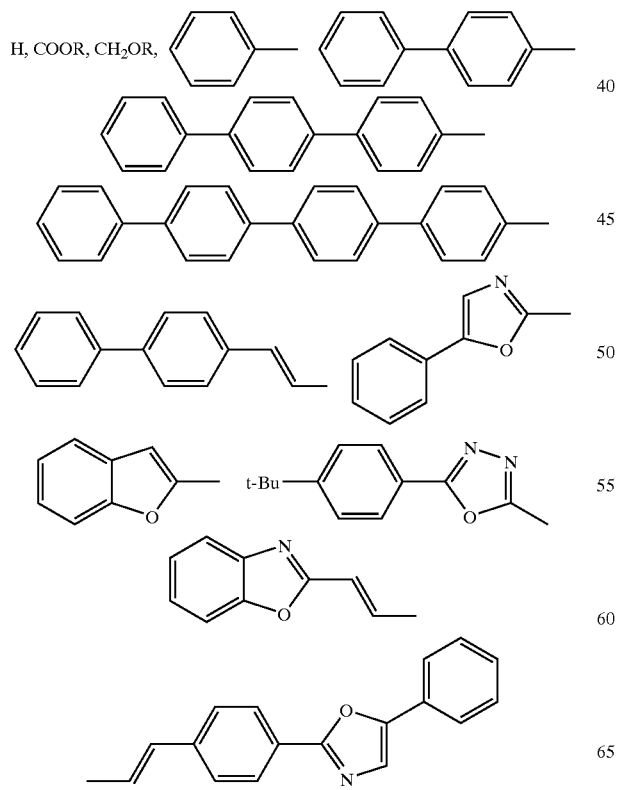
-continued
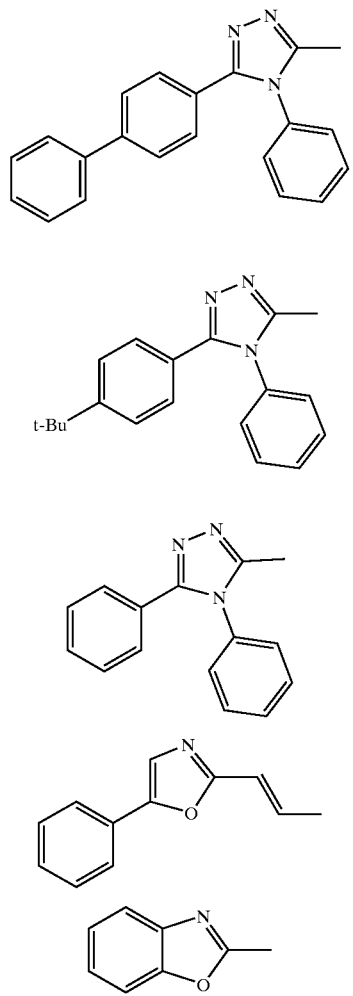
And Q, P1 are identical or different and selected from the group
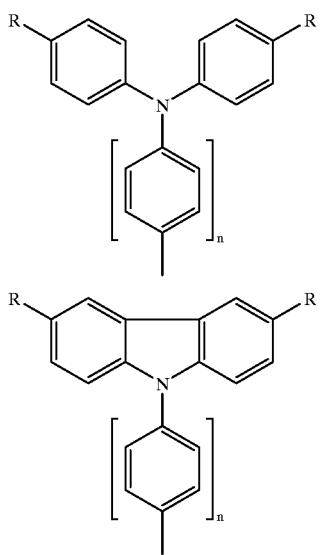

-continued
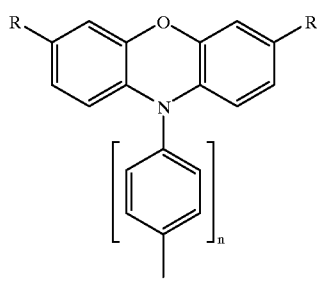
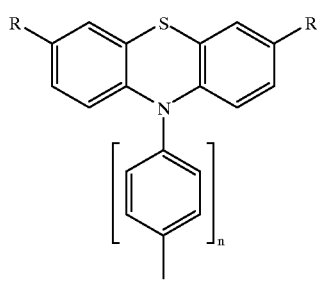
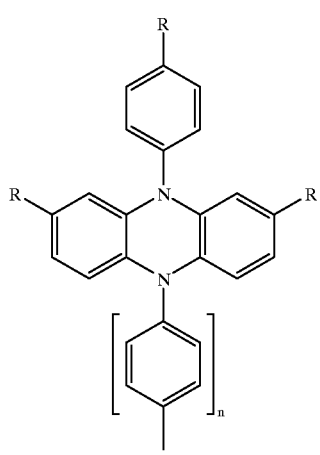
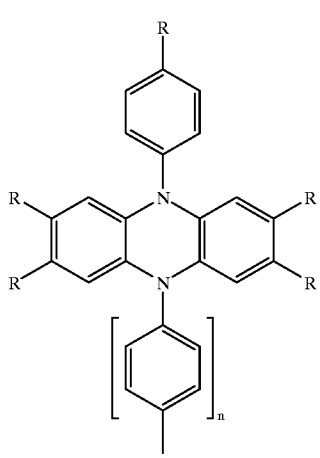
-continued
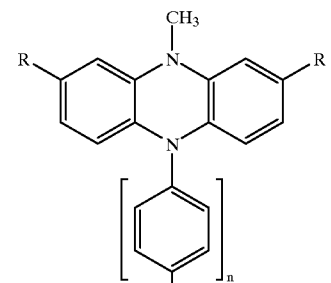
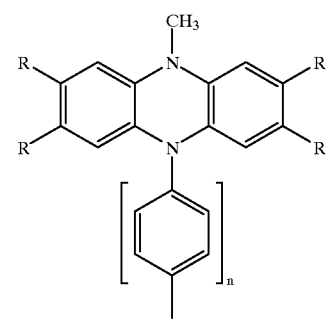
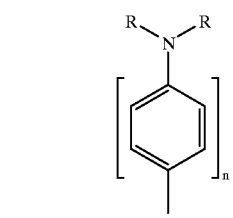
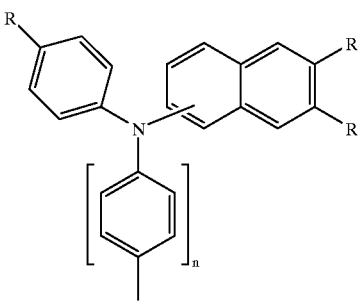
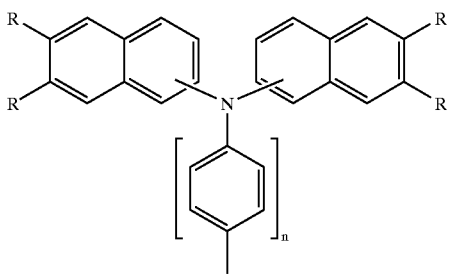
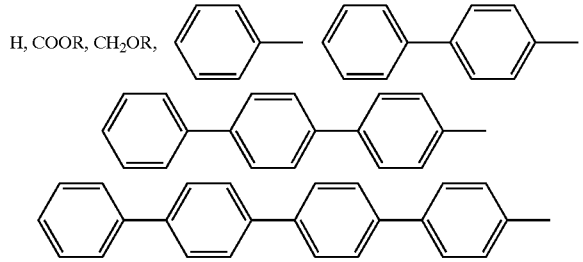

-continued
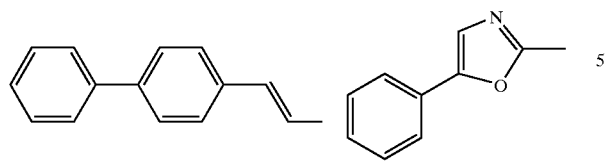
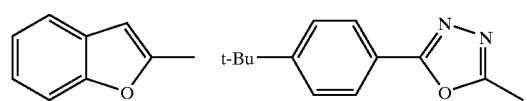
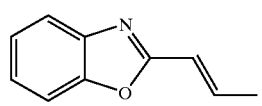
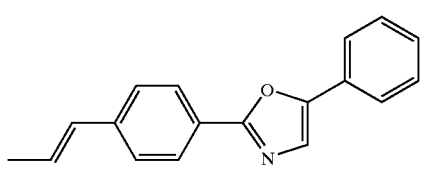
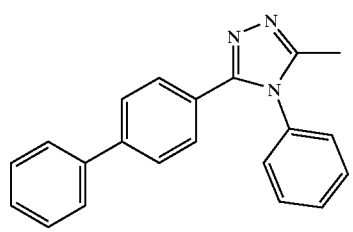
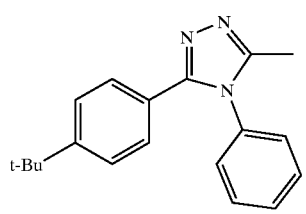
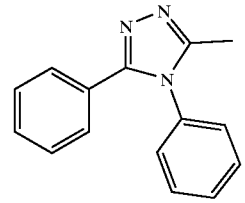
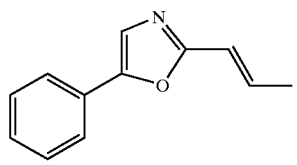
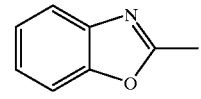
wherein the symbols and indices have the meaning as specified above;
4.c) $K^1$=M and is selected from the group
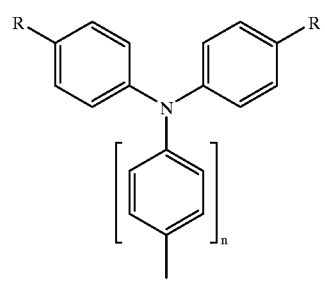
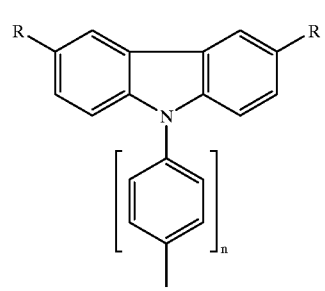
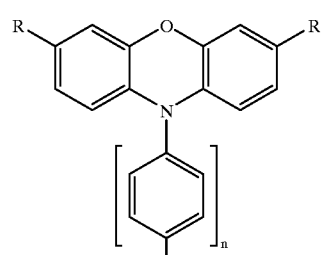
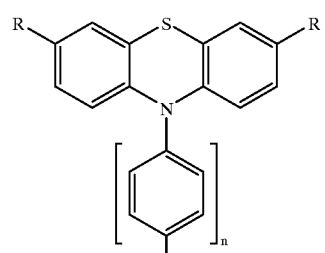
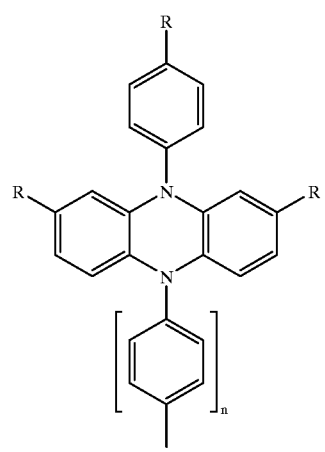

-continued
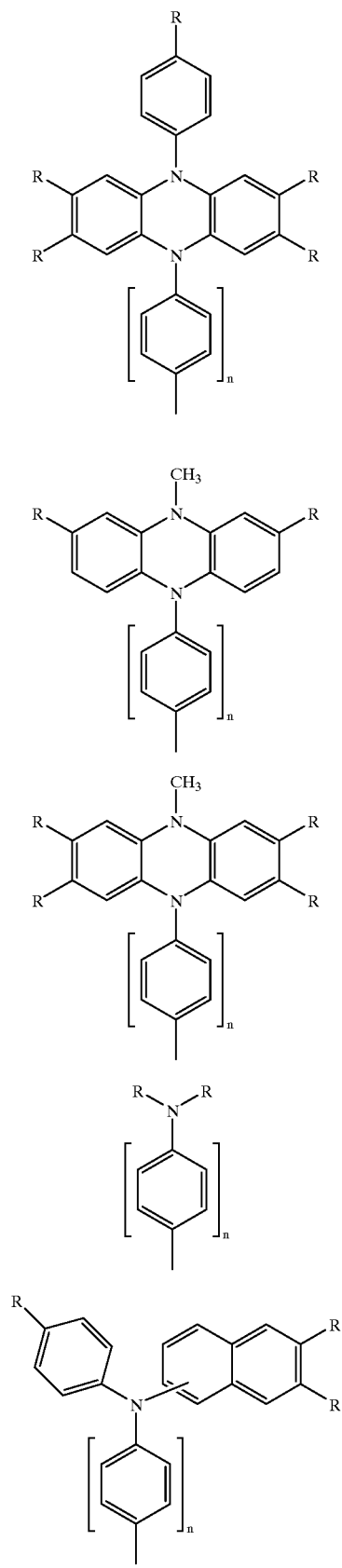
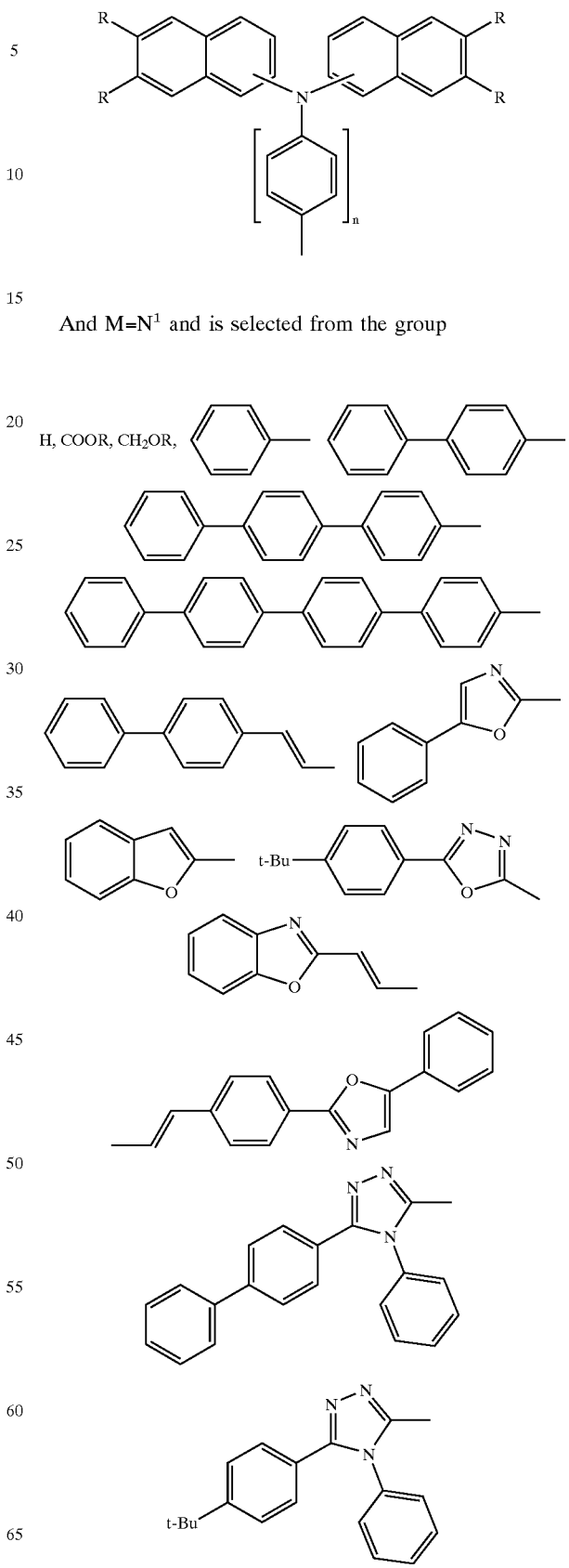
And M=N[1] and is selected from the group
H, COOR, CH$_2$OR,

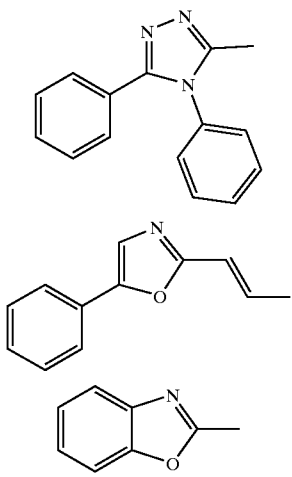
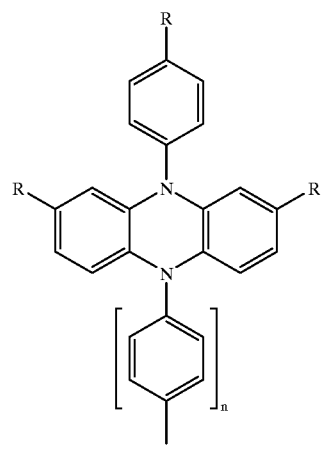
And Q, P¹ are identical or different and selected from the group
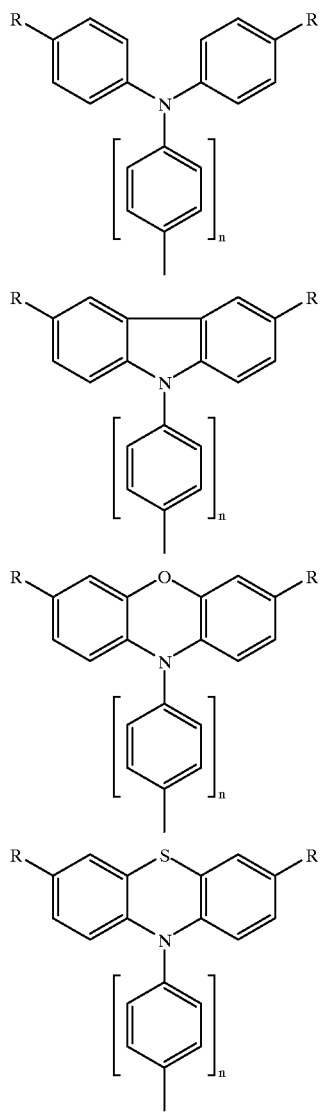
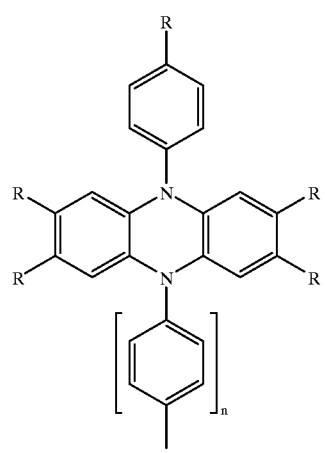
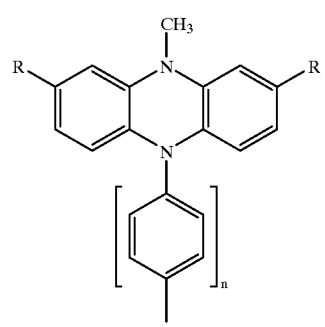
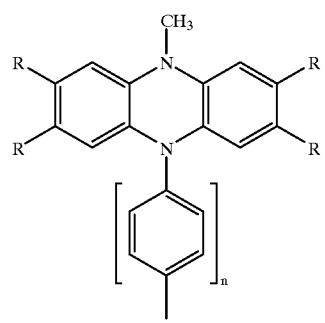

-continued
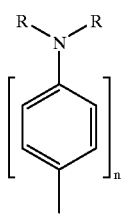
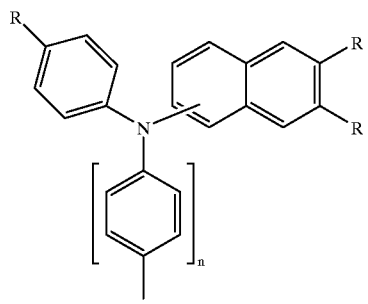
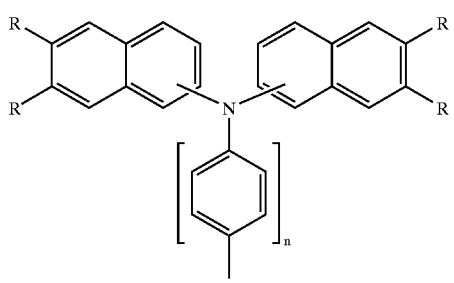
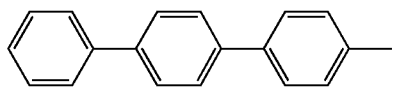
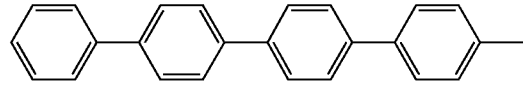
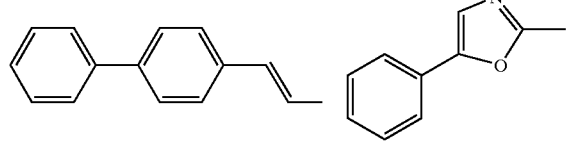
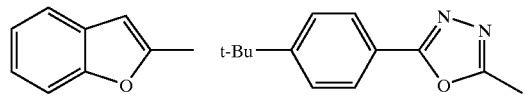
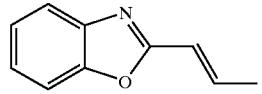
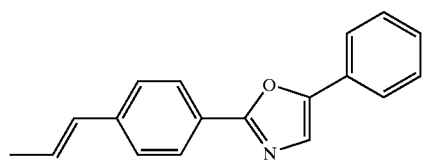
-continued
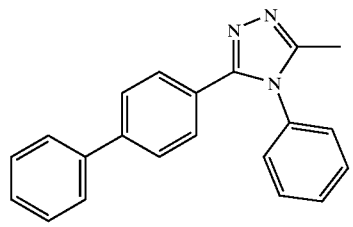
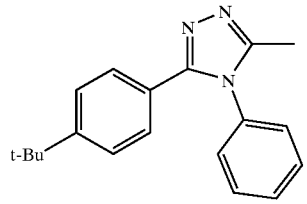
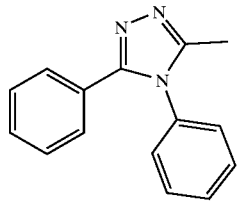
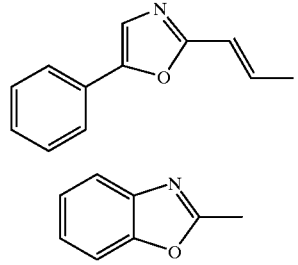
Wherein the symbols and indices have the above specified meaning.
More preferred are the following compounds according to formula (4):
4.aa) $K^1=L=M=N^1$ and is selected from the group:
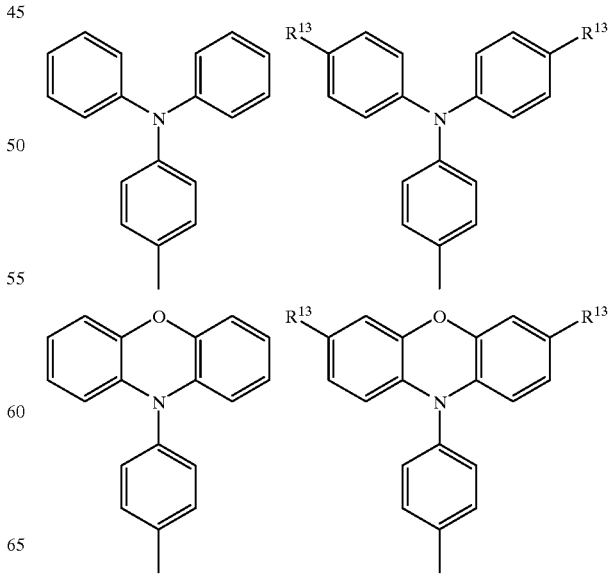

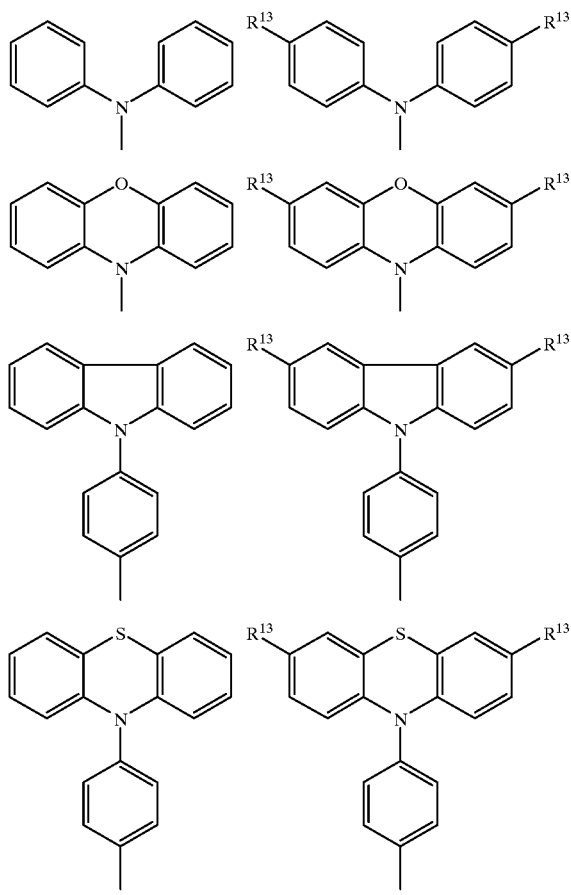
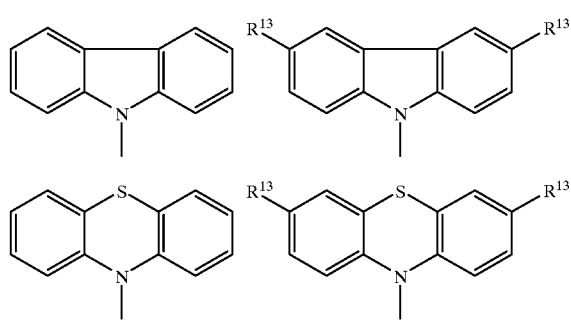
Wherein R13 means —O—CH3, —O—C2H5, —S—CH3, —S—C2H5, preferably —O—CH3, —S—CH3, more preferred —O—CH3;
and Q=P and is selected from the group
H, COOR$^{14}$, CH$_2$OR$^{14}$,
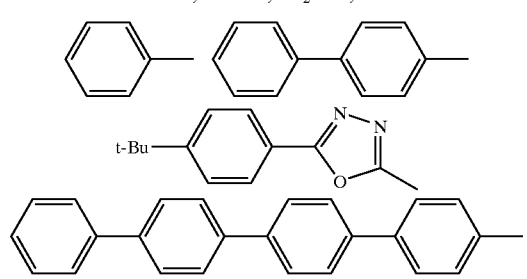
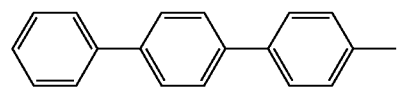
wherein R14 is a linear or branched alkyl group with 1 to 12, preferably 1 to 4 C atoms;
4.ba) K$^1$=L=M=N$^1$=Q=P$^1$ and is selected from the group
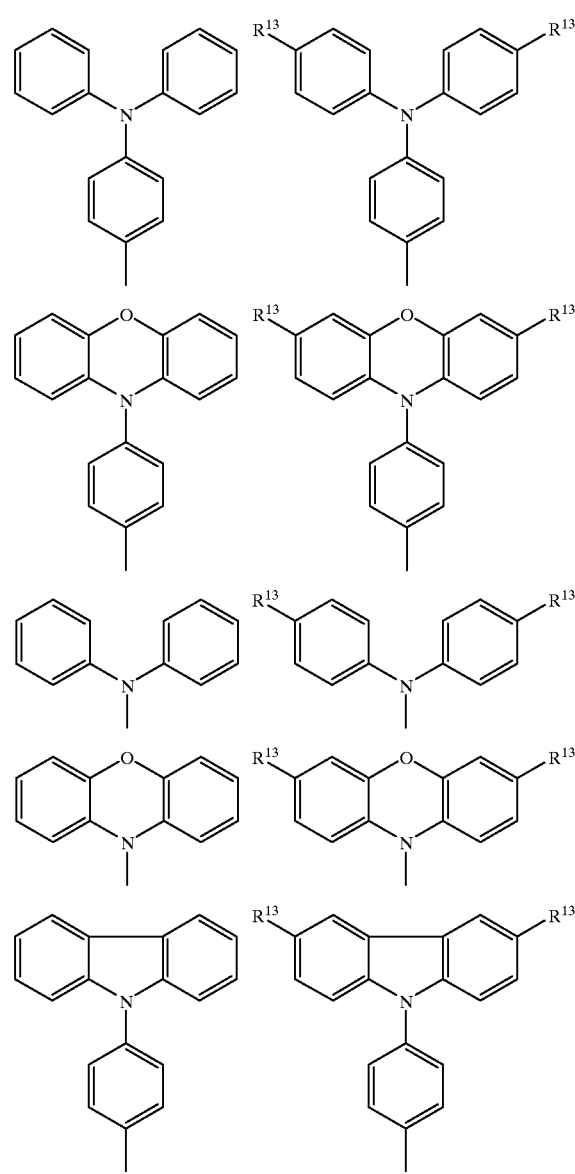
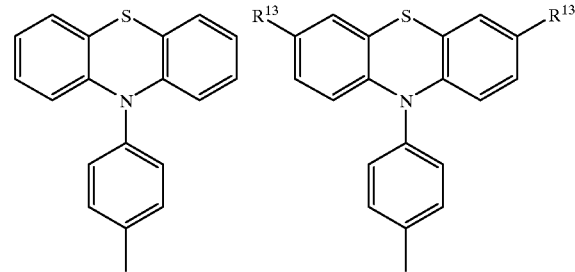

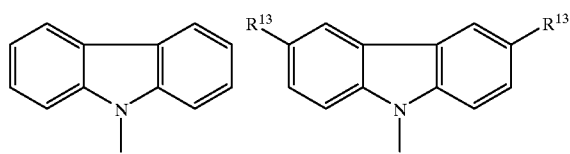

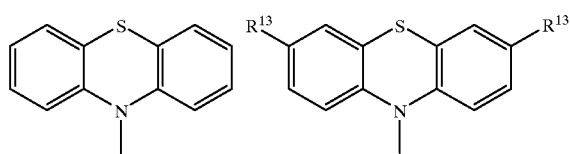

Wherein R13 has the above specified meanings;

4.ca) $K^1=L=M=N^1$ and is selected from the group

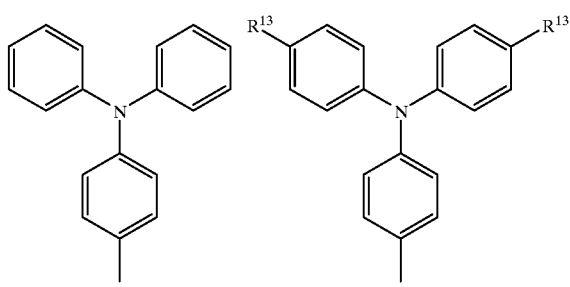

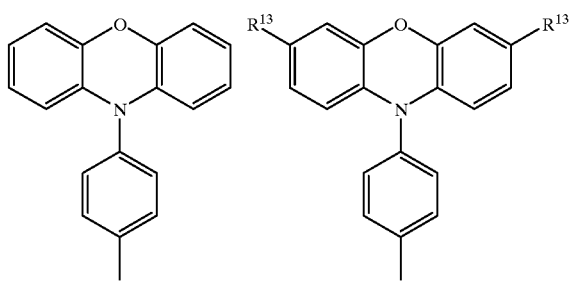

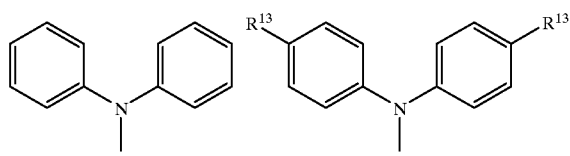

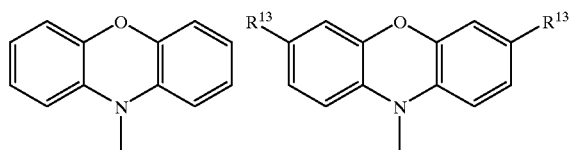

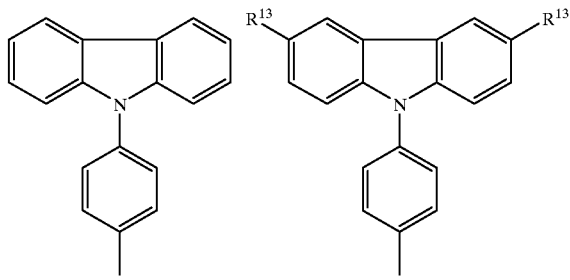

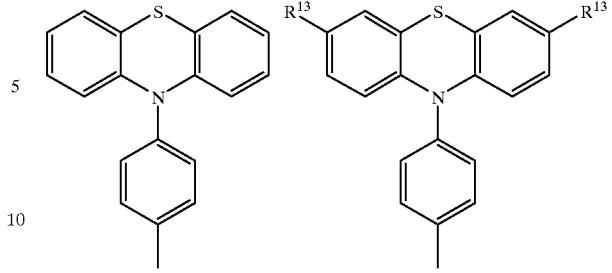

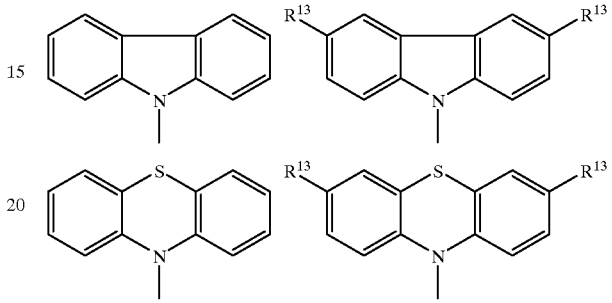

And Q=H and $P^1$ is selected from the group

H, $COOR^{14}$, $CH_2OR^{14}$,

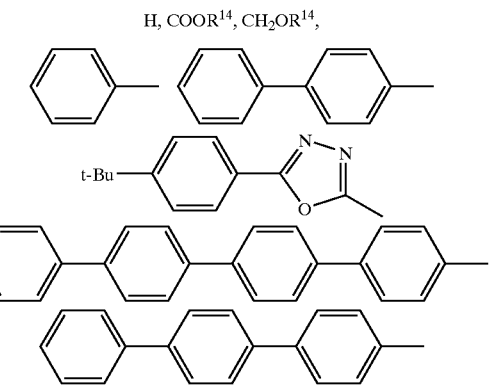

Wherein $R^{13}$, $R^{14}$ have the above specified meaning.

Further organic hole transporting agents are disclosed in EP 0 901 175 A2 the disclosure of which is herein incorporated by reference. More particularyl, EP 0 901 175 A2 dislcoses organic hole conducting agents which include aromatic diamine compounds having connected tertiary aromatic amine units of 1,-bis(4-(di-p-tolylamino)phenyl)-cyclohexane as described in JP-A 194393/1984, aromatic diamines containing two or more tertiary amines and hjaving two or more fused aromatic rings substituted on the nitrogen atoms as typified by 4,4-bis[(N-1-naphthyl)-N-phenylamino]-biphenyl as described in JP-A 234681/1983, aromatic trimers having a start burst structure derived from triphenylbenzene as described in U.S. Pat. No. 4,923,774, aromatic diamines such as N,N'-diphenyl-N,N'-bis(3-methyphenyl)-(1,1'-biphenyl)-4,4'diamine as described in U.S. Pat. No. 4,764,625, α,α,α',α'-tetramethyl-α,α'-bis(4-di-p-tolylaminophenyl as described in JP-A269084/1991, triphenylamine derivatives whose molecule is sterically asymmetric as a whole as desribed in JP-A 129271/1992, compounds having a plurality of aromatic diamino groups substituted on a pyrenyl group as described in JP-A 175395/1992, aromatic diamines having teriary amine units connected through an ethylene group as described in JP-A 264189/1992, aromatic diamines having a styryl structure as described in JP-A 290851/1992, star burst type aromatic triamines as described in JP-A 308688/1992, benzyl-phenyl compounds as described in JP-A 364153/1992, compounds having tertiary amine units connected through a fluorene group as described in JP-A 25473/1993, triamine compounds as described in JP-A 239455/1993, bisdipyridylaminobiophenyl compounds as described in JP-A 320634/1993, N,N,N-triphenylamine derivatives as described in JP-A 1972/1994, armatic diamines having a phenoxazine structure as described in JP-A 290728/1993, diaminophenylanthridine derivatives as described in JP-A 45669/1994, and other carbazole derivatives.

Other hole transporting agents which are disclosed in EP 0 901 175 and which may be used in the present invention, include hydrazoen compounds (JP-A 311591/1990), silazane compounds (U.S. Pat. No. 4,950,950), silanamine derivatives (JP-A 49079/1994), phosphamine derivatives (JP-A 25659/1994), quinacridone compounds, stilebene compounds such as 4-di-p-tolylamino-stilbene and 4-(di-p-tolylamino)-4'-[4-di-p-tolylamino)-styryl]stilbene, triazole derivatives, oxadiazole derivatives, imidazole derivatives, polyarylalkane derivatives, pyrazoline derivatives, pyrazolone derivatives, oxadiazole derivatives, imidazole derivatives, polyarylalkane derivatives, pyrazoline derivatives, amino-substituted chalcone derivatives, oxazole derivatives, styrylanthracene derivatives, fluorenone derivatives and polysilane derivatives. These compounds may be used alone or in admixture of two or more. The same applies also to the other compounds disclosed herein, including those incorporated herein by reference.

In addition to the aforementioned compounds, polymers can be used as the hole transporting agents. Useful polymers include polyvinyl carbazole and polysilanes (Appl. Phys. Lett., vol. 59, 2760, 1991), polyphosphazenes (JP-A 310949/1993), polyamides (JP-A 10949/1993), polyvinyl triphenylamine (Japanese Patent Applicaiton No. 133065 (1993), polymers having a triphenylamine sleketon (JP-A 133065/1992), polymers having triphenylamine units connected through a emthylene group (Synthetic Metals, vol 55–57, 4163, 1993) and polymethacrylates containing aromatic amine (J.Polym. Sci., Polym. Chem. Ed., vol 21, 969, 1983). When polymers or mixtures thereof are used as the hole transporting agent, they preferably have a number average molecular weight of at least 1,000, more preferably at least—5,000. Preferred illustrative non-limiting examples of the organic hole transporting compound are given below.

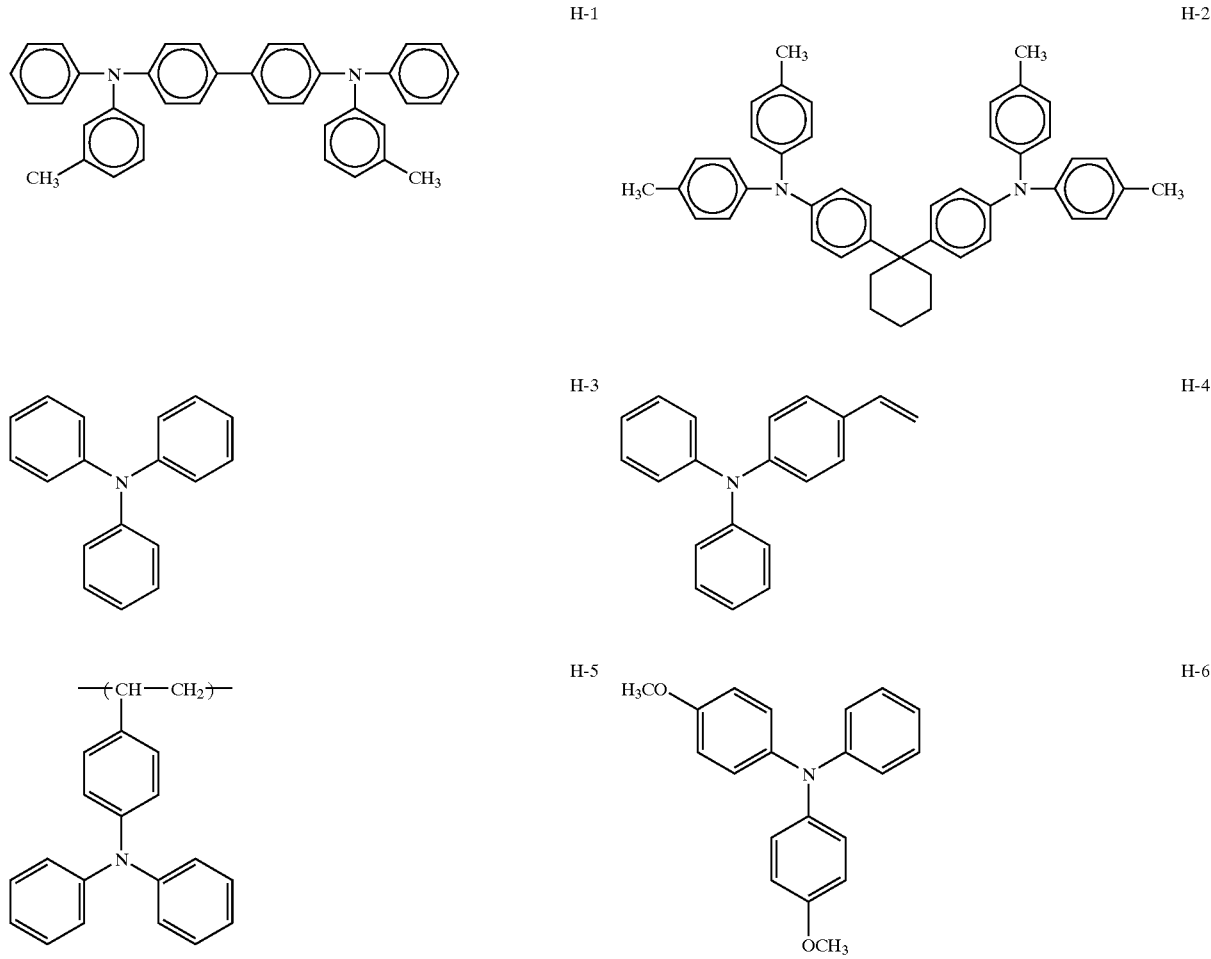

-continued
H-7
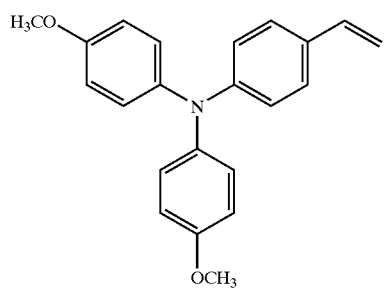
H-8
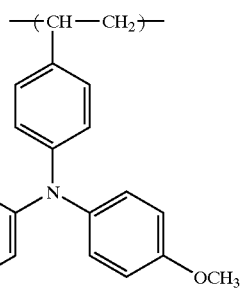
H-9
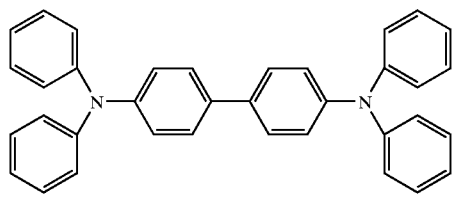
H-10
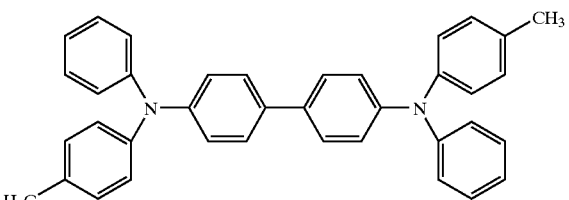
H-11
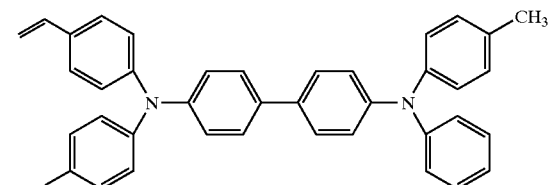
H-12
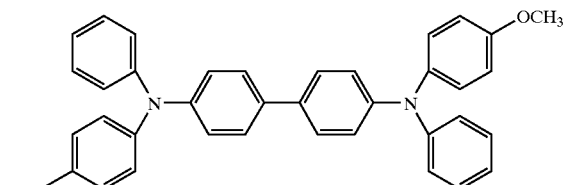
H-13
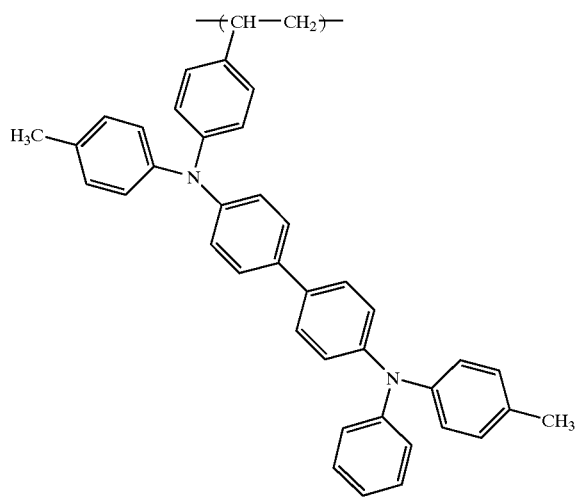
H-14
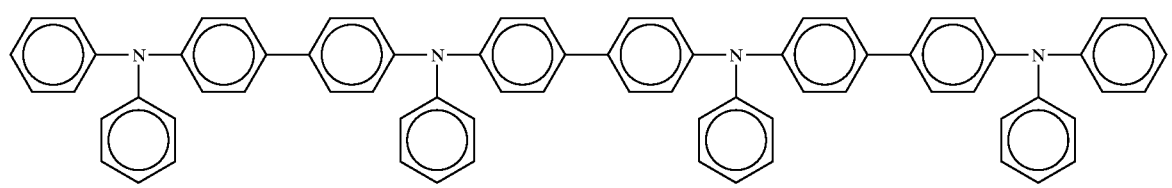
H-15
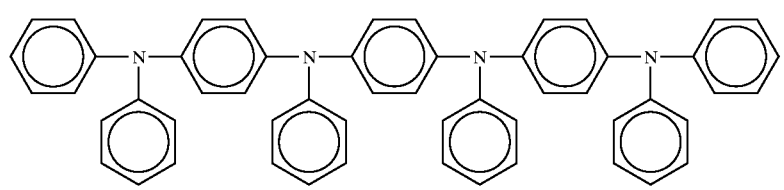

-continued
H-16
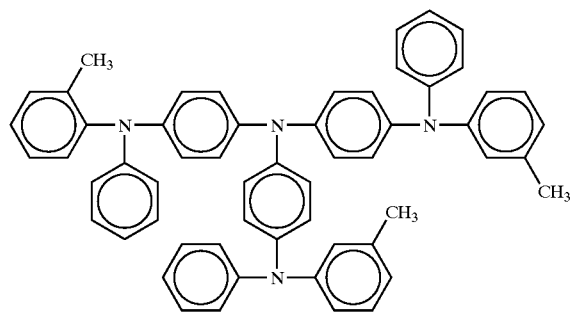
H-17
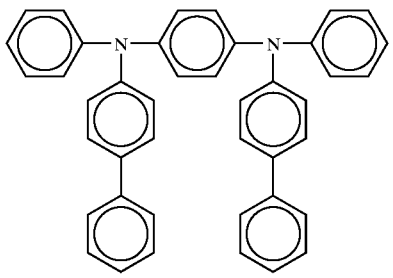
H-18
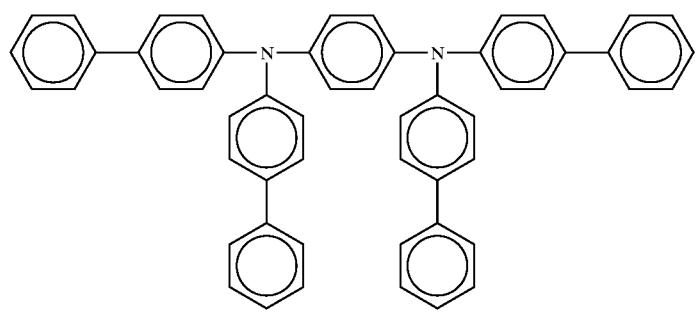
H-19
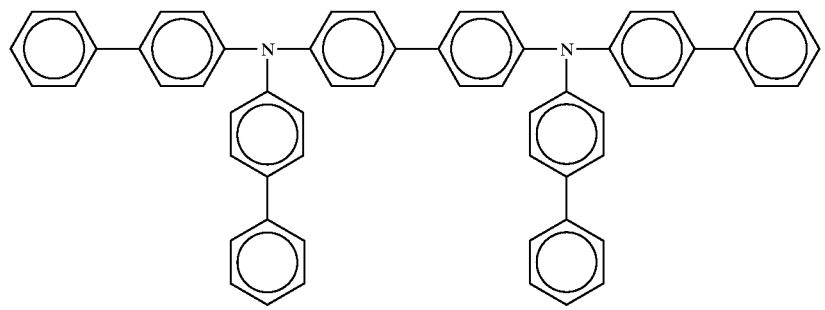
H-20
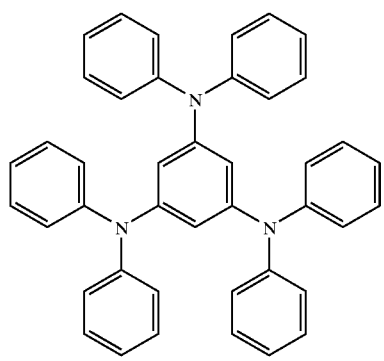
H-21
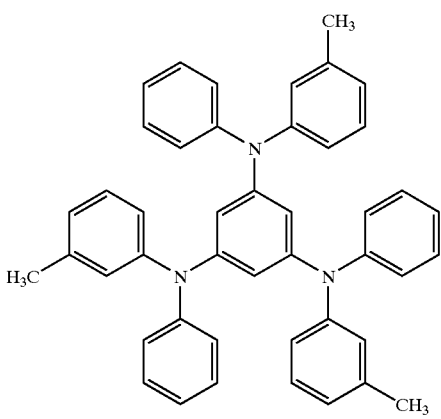

-continued
H-22
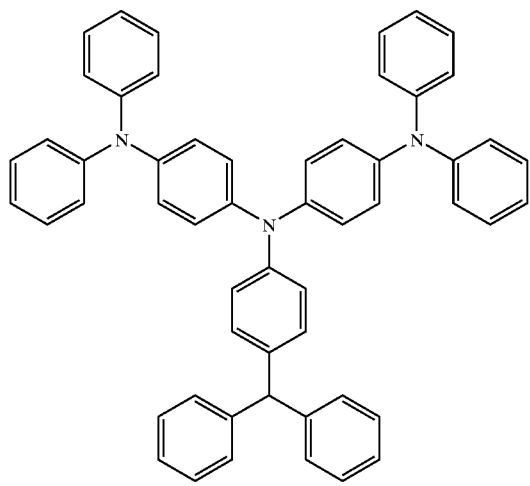
H-23
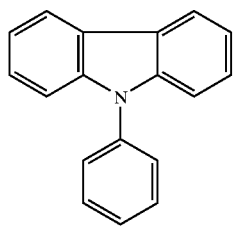
H-24
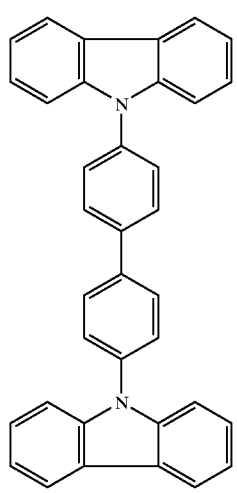
H-25
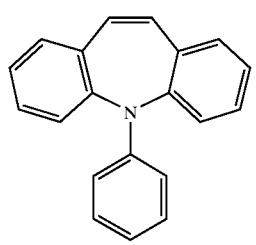
H-26
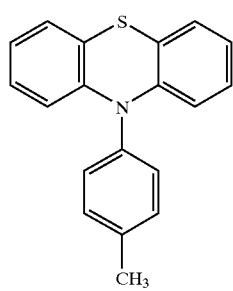
H-27
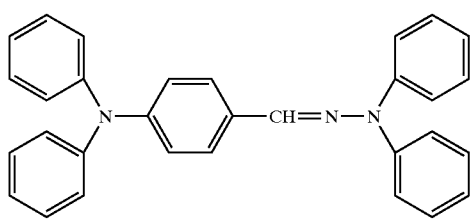
H-28
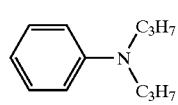
H-29
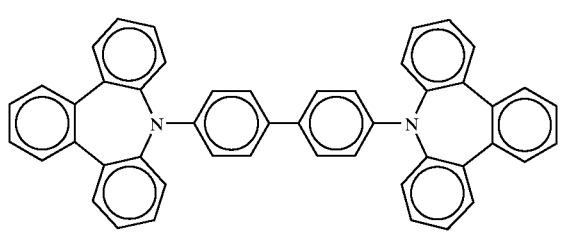

-continued
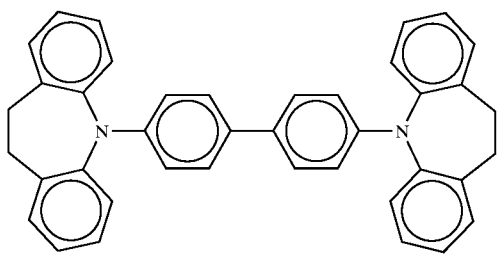 H-30
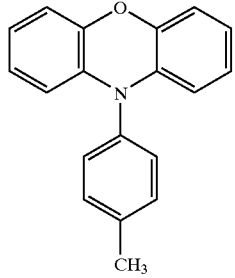 H-31
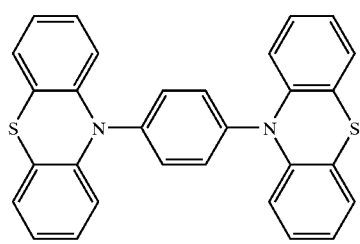 H-31
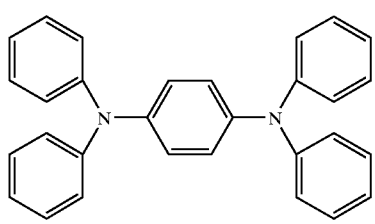 H-32
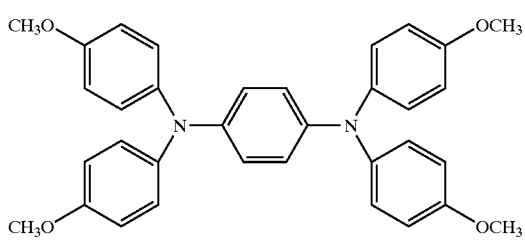 H-34
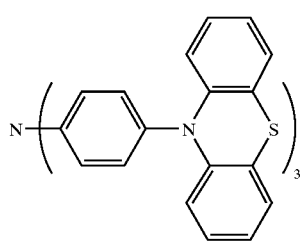 H-35
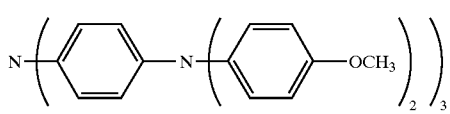 H-36
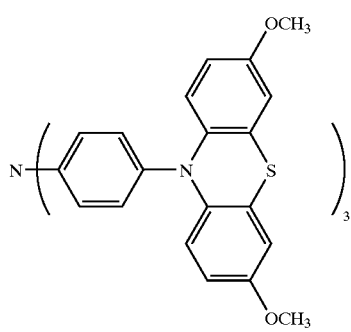 H-37
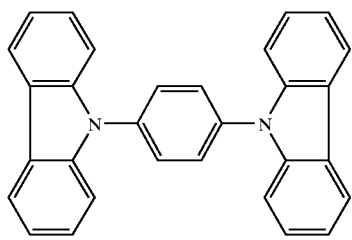 H-38
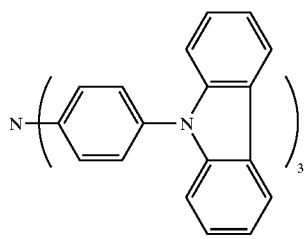 H-39
Further possible organic hole transporting agents are described in DE 197 04 031 A1 and incorporated herein by reference which might be used either alone or in any combination thereof. More particularly, an aromatic tertiary amino compound A is disclosed which is characterized by any of the structural formulae (5) to (8).

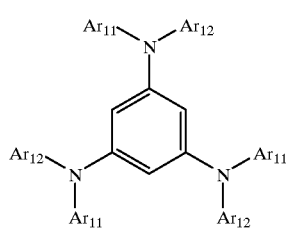
(5)

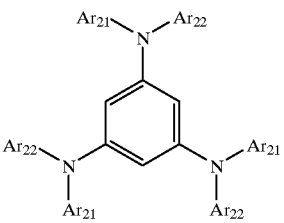
(6)

wherein Ar11 and Ar12 may be identical or different and may represent the following group of aryl compounds:

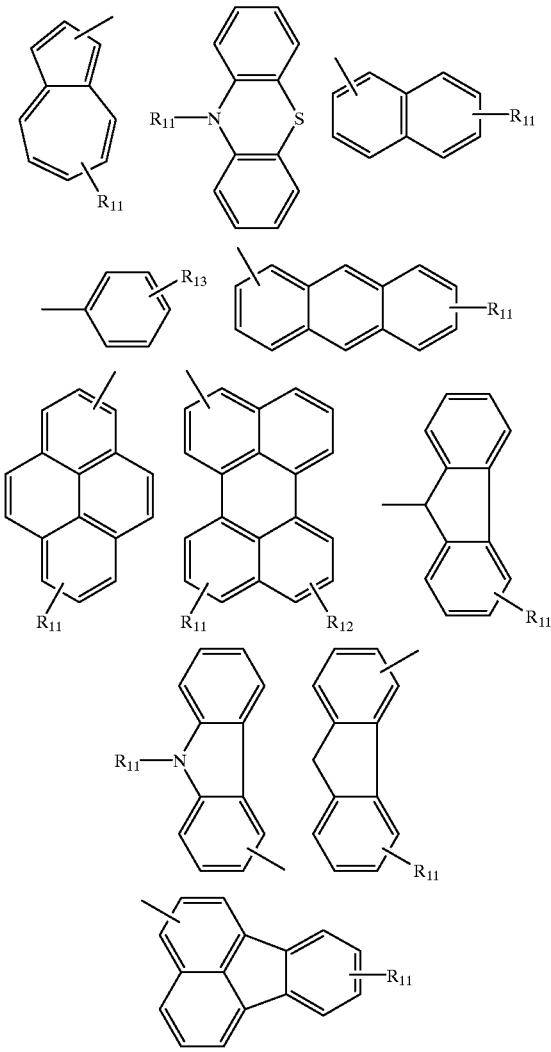

wherein 11 and R12 may be identical or different and represent hydrogen, optionally substituted C1 to C10 alkyl, alkoxy, phenoxy, phenyl, alkyl substituted phenyl, alkoxy substituted phenyl, aryl, halogen or dialkylamino, and wherein R13 optionally represents substituted C2 to C8 alkyl, alkoxy, phenoxy, phenyl, alkyl subsituted phenyl. Alkoxy substituted phenyl, aryl, dialkylthiolate, diarylthiolate or dialkylamino.

wherein Ar21 and Ar 22 represents

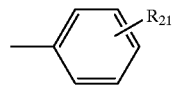

and wherein R21 represents optionally substituted C2 to C10 alkyl, alkoxy, phenoxy, alkyl-subsituted phenyl, alkoxy substituted phenyl, aryl, aralkyl or dialkylamino.

(7)

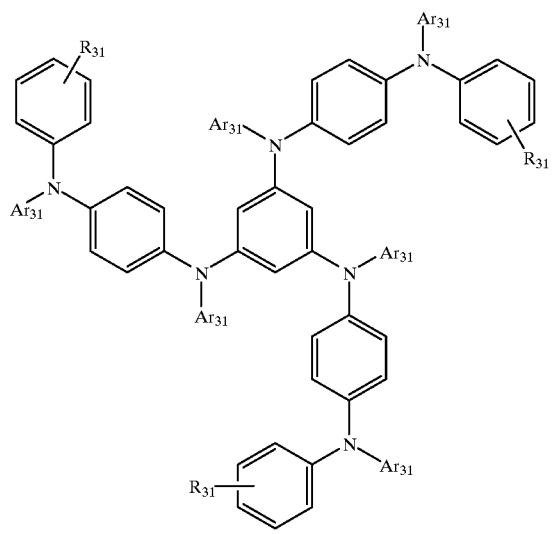

Wherein Ar 31 represents the subsequent group of aryl compounds

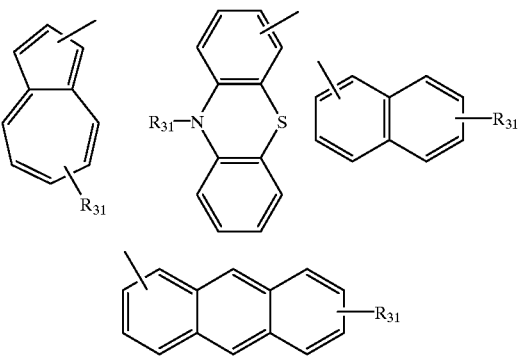

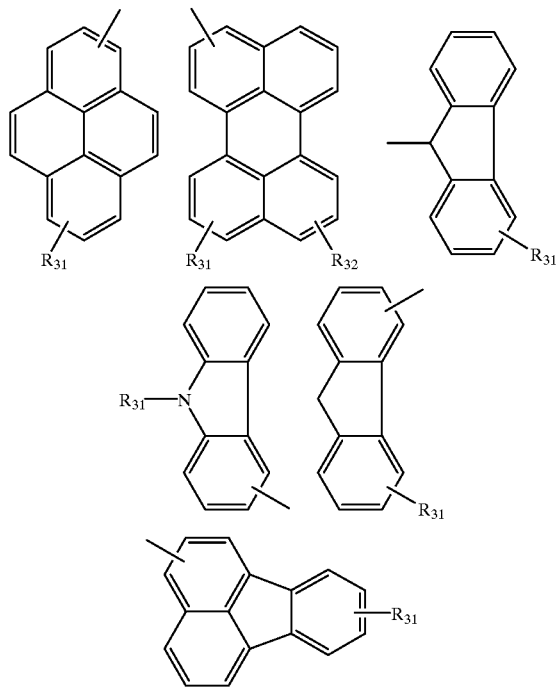

wherein R31 and R32 may be identical or different and represent
hydrogen, optionally substituted C1 to C10 alkyl, alkoxy, phenoxy, phenyl, alkyl subsituted phenyl, alkoxy subsituted phenyl, aralkyl, aryl, halogen or dialkylamino, (8)

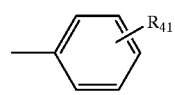

wherein Ar41 represents and wherein R4 represents optionally subsituted C1 to C10 alkyl, alkoxy, phenoxy, phenyl, alkyl substituted phenyl, alkoxy subsituted phenyl, aralkyl, aryl, halogen or diaminoalkylamino.

As indicated already above the guidelines disclosed herein apply not only to single organic electrically conducting agents but also to mixtures thereof. As also disclosed herein, sometimes the mixture of at least two organic electrically conducting agents which per se do not necessarily fulfil at least one of the above guidelines, may do so.

Possible compounds of that type are derivatives of triphenyldiamine are such as the one represented by formula (I)

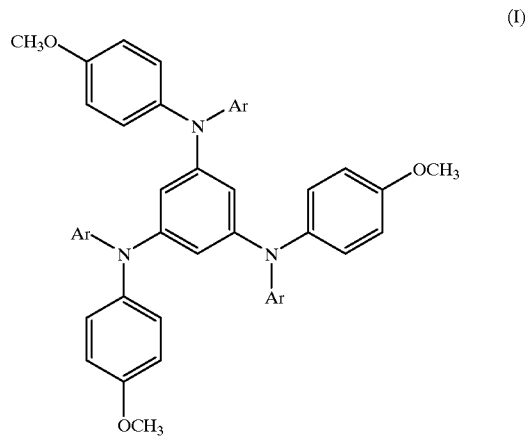

wherein Ar is a susbtituent according to formula (II)

(II)

which is referred to as MH-TDAB (tris(methoxyphenyl hexyloxy phenyl amino)benzene, and the one represented by formula (III)

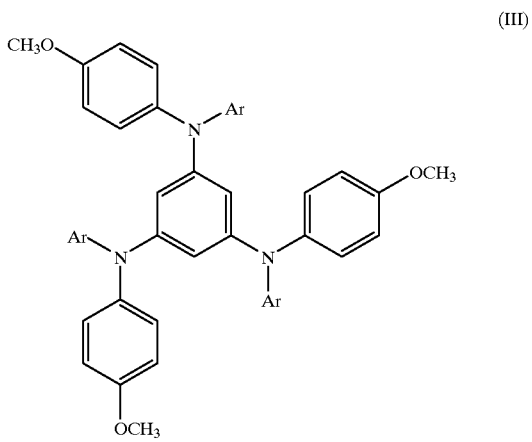

Wherein Ar is a substituent represented by formula (IV)

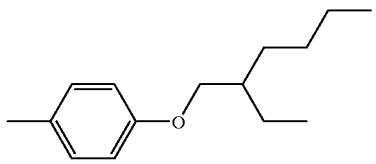
(IV)

which is referred to as MEH-TDAB (Tris(methoxyphenyl ethylhexyloxy phenyl amino)benzene).

Additionally it is to be noted that certain mixtures of the MH-TDAB and MEH-TDAB exhibits a Tg which allows to use such a mixture as the organic electrically conducting agent as will be shown in the examples.

The use of dopants in dye-sensitized solar cells is well known. Dopants can increase short circuit currents up to an order of magnitude. Besides Li salts electron acceptors may be used for such purposes. A dopant preferably added to the organic electrically conducting agent and thus to the inventive photoelectric conversion device is tris(p-bromo phenyl) aminium hexachloroantimonate as represented by formula (V):

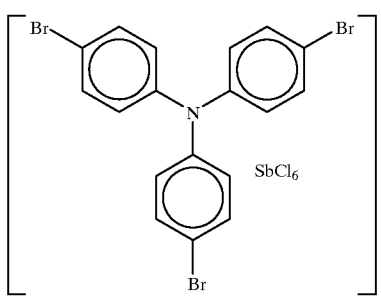
(V)

Other dopants which may be used are the following ones:
2,3,5,6-Tetrafluoro-7,7,8,8-tetracyanoquinodimethane (F4-TCNQ)

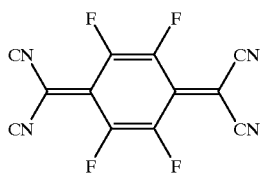
(VI)

Nitrosonium-tetrafluorborat (BF$_4$NO)
and the following compounds represented by their structures

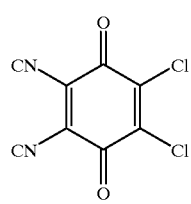
(VII)

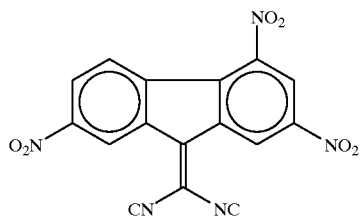
(VIII)

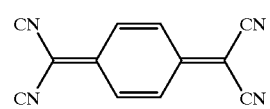
(IX)

Further dopants being general electron acceptors, are known to the one skilled in the art.

Dyes which can be used for sensitizing the semiconductor are known in the art such as EP 0 887 817 A2 the disclosure of which is incorporated herein by reference. Among the dyes to be used in the photoelectric conversion device are also Ru (II) dyes such as Ru 535 cis-bis(isothiocyanato)bis (2,2'-bipyridyl-4,4'-dicarboxylato)-ruthenium (II) and Ru 535 cis-Di(thiocyanato) bis (2,2'-bipyridyl-4,4'-dicarboxylate) ruthenium (II) tetrabutylammonium bis-TBA or complexes of other transition metals of the metal type (L3).

Ru620 (black dye): Tris(isothiocyanato)-ruthenium(II)-2, 2':6',2"-terpyridine-4,4',4"-tricarboxylic acid
Ru470: tris(2,2'bipyridyl-4,4'dicarboxylato) ruthenium (II) dichloride
Ru505: cis-bis(isocyanato) (2,2'bipyridyl-4, 4'dicarboxylato) ruthenium (II).

The dyes used to sensitize the semiconductor may be attached thereto by chemisorption, adsorption or by any other suitable ways.

The semiconductor used in the inventive photoelectric conversion device is preferably a nanoparticulate one. The material can be a metal oxide and more preferably an oxide of the transition metals or of the elements of the third main group, the fourth, fifth and sixth sub-group of the periodic system. These and any other suitable materials are known to those skilled in the art and are, e.g., disclosed in EP 0 333 641 A1 the disclosure of which is incorporated herein by reference.

The semiconductor material may exhibit a porous structure. Due to this porosity the surface area is increased which allows for a bigger amount of sensitizing dye to be immobilized on the semiconductor and thus for an increased performance of the photoelectric conversion device. Additionally, the rough surface allows the trapping of light which is reflected from the surface and directed to neighbouring surfaces which in turn increases the yield of the light.

Figure 7:
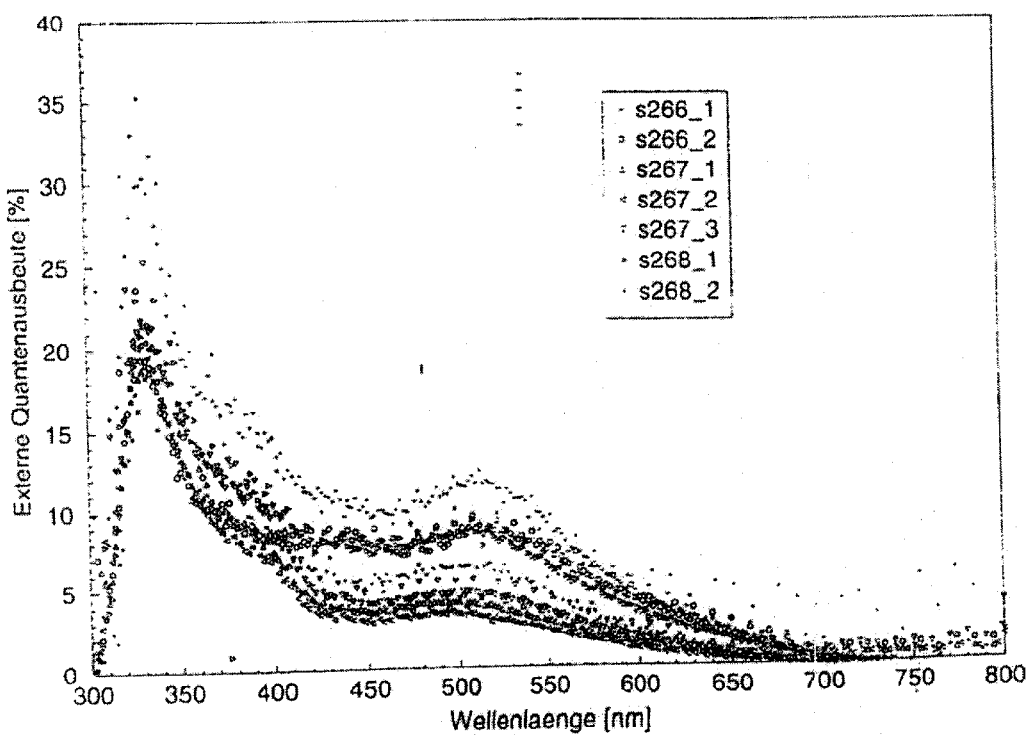

For example, the TiO$_2$ particles have a diameter of about 10 nm; the morphology is anastase. The porous structure of the semiconductor material is illustrated in FIG. 7 showing a SEM image.

Figure 2:
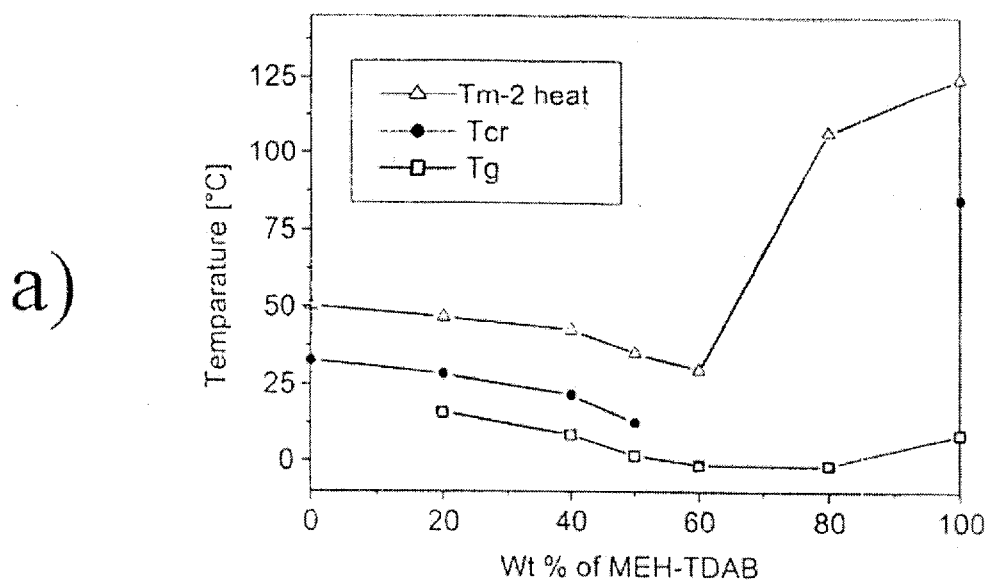
Figure 2:
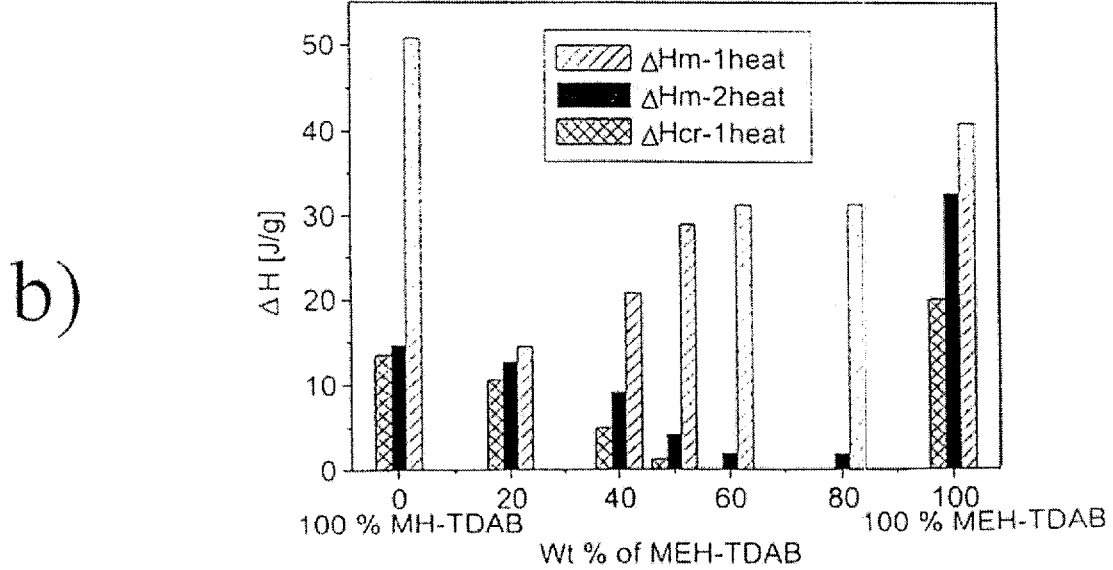
Figure 3:
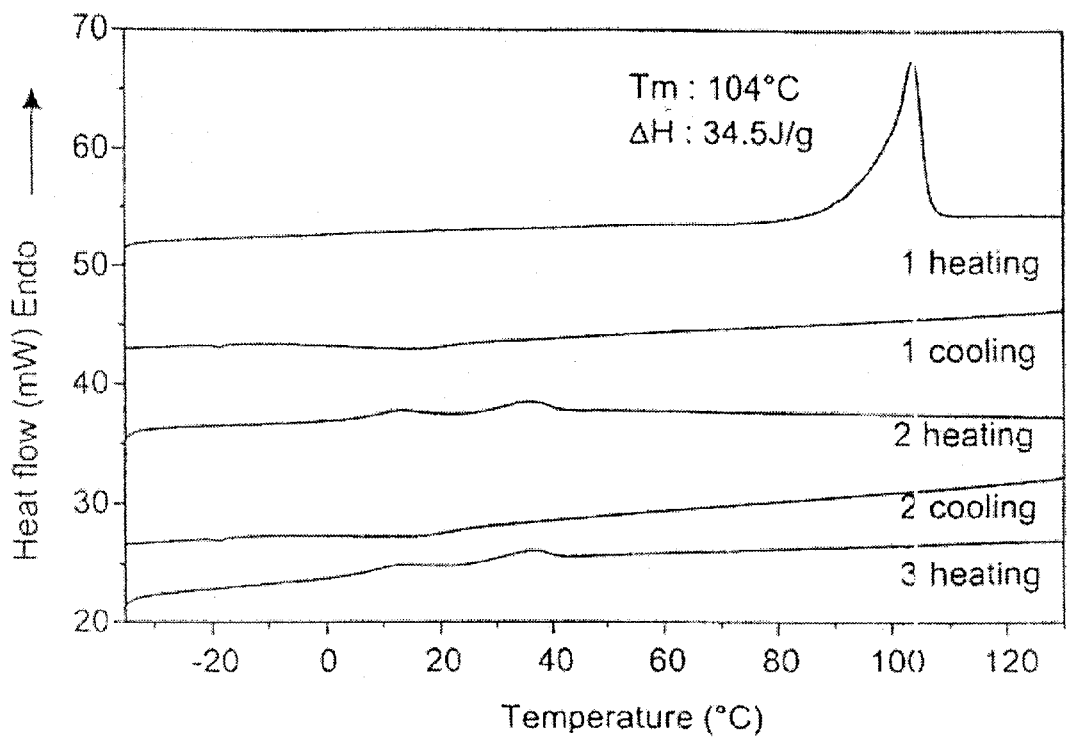
Figure 4:
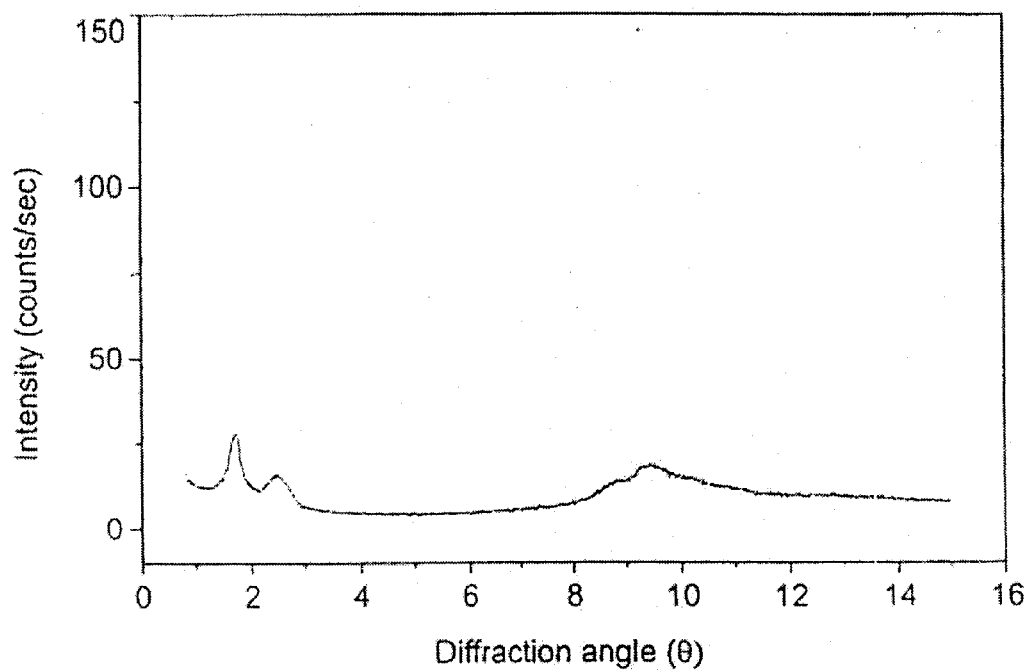
Figure 5:
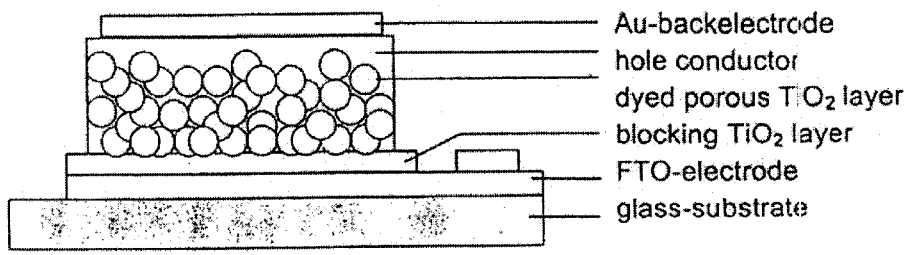
Figure 6:
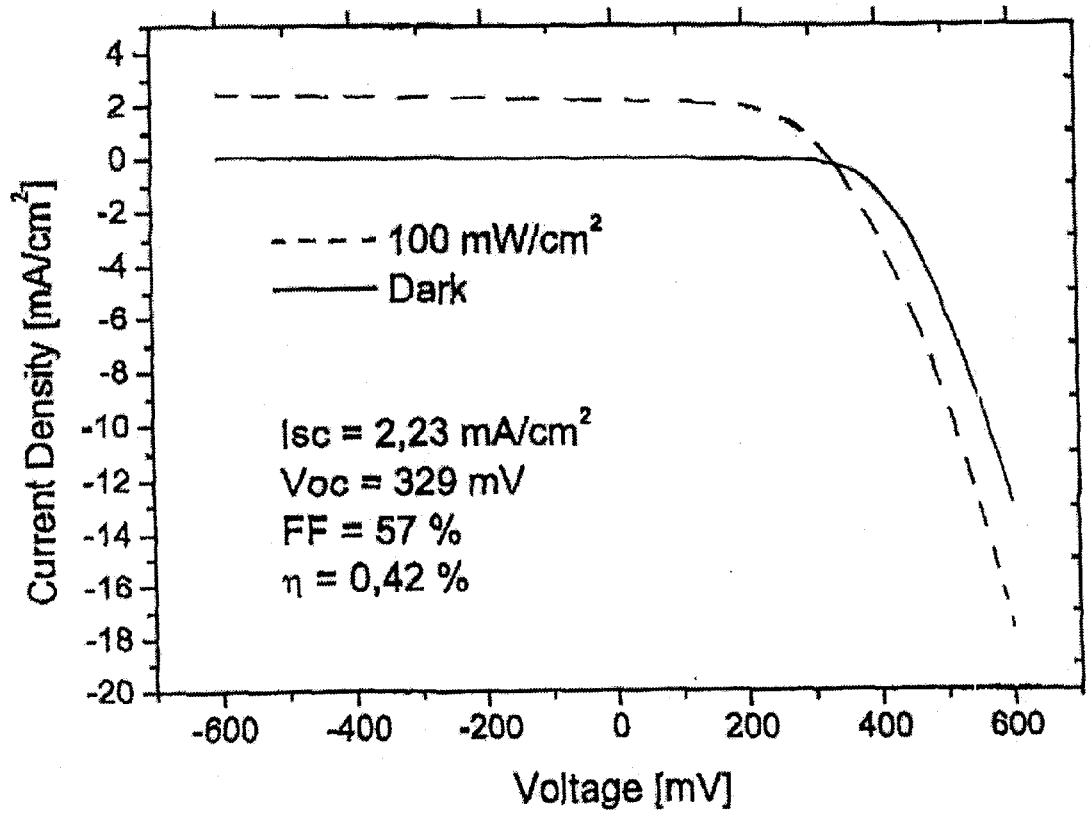
Figure 8:
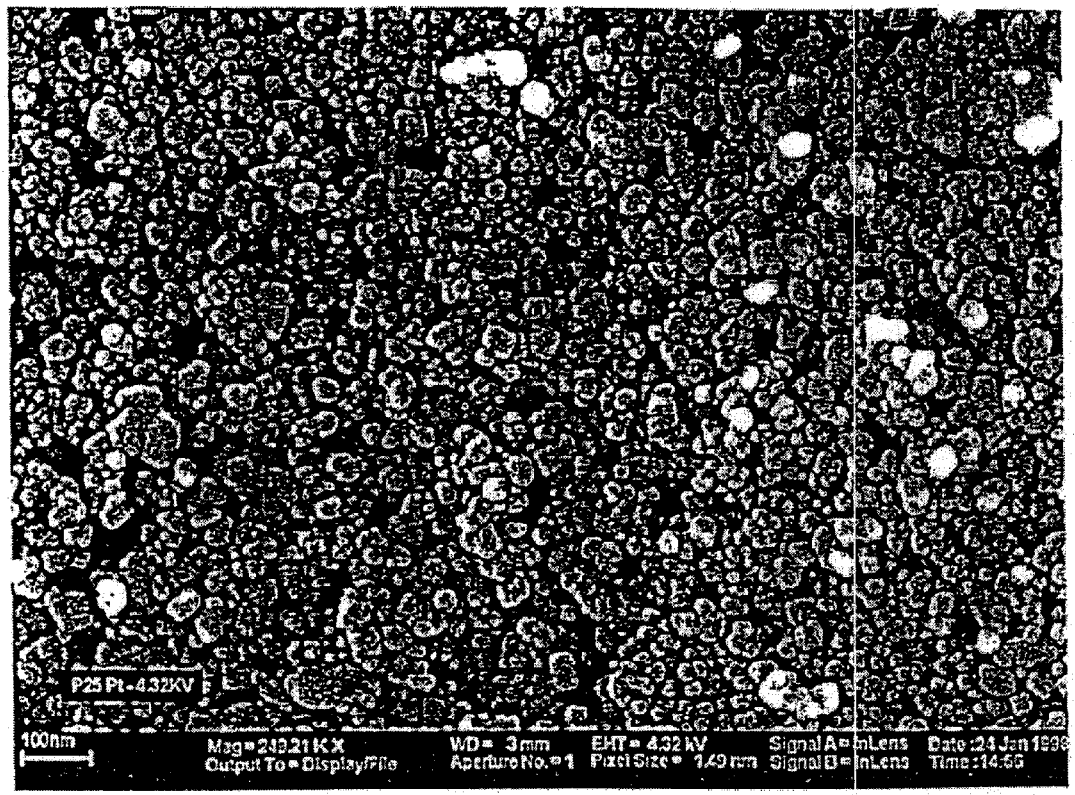
Figure 9:
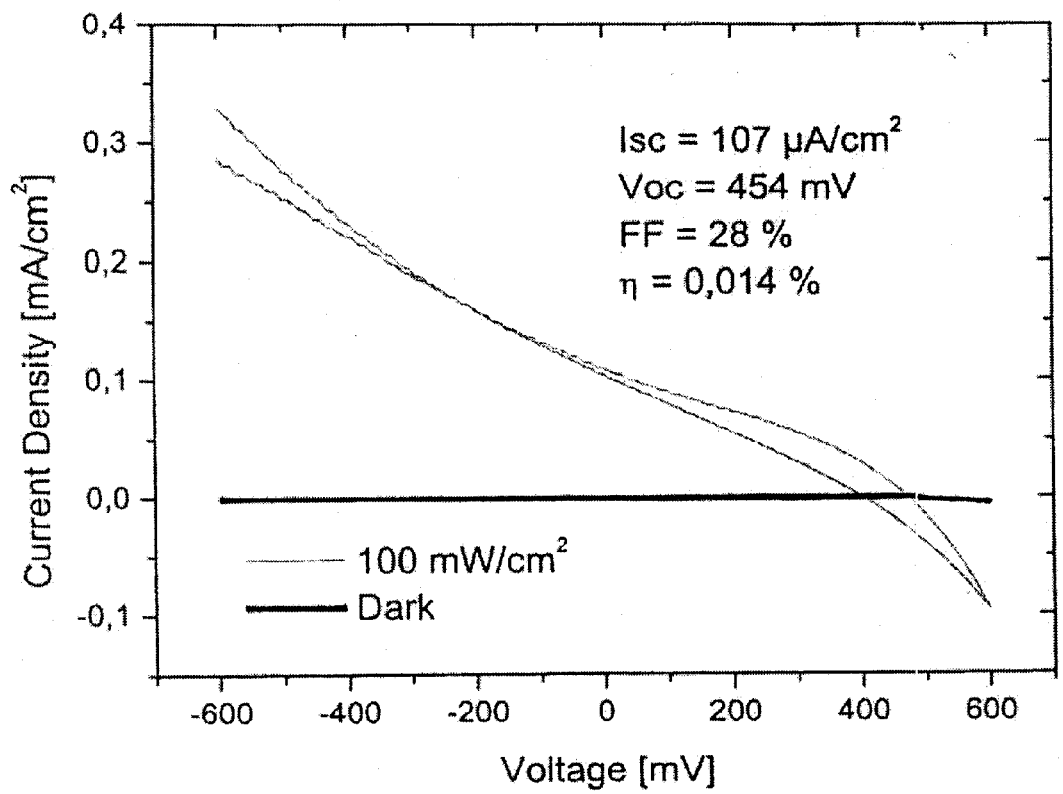
Figure 10:
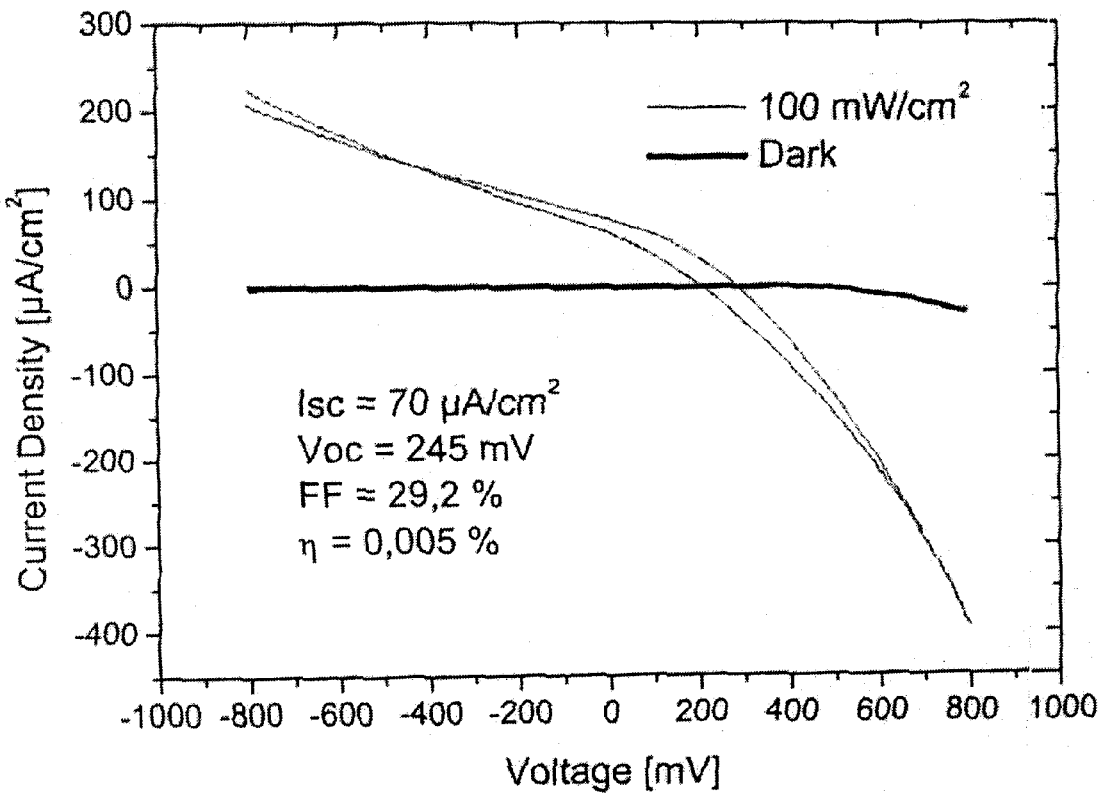
Figure 11:
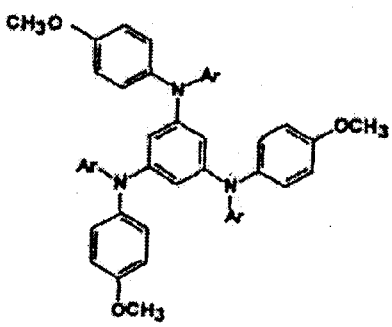
Figure 12:
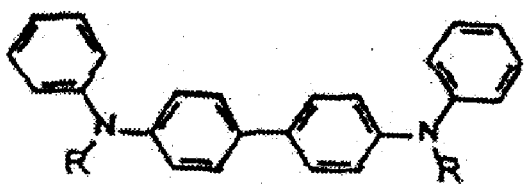

The method for the manufacture of a photoelectric conversion device can be summarized as follows.
  I. Structuring of FTO Substrates
    a. Cover the parts of the substrate where FTO should remain with scotch tape
    b. Put the substrate in a petri dish and cover with Zn granulate
    c. Apply a few drops of 4 N HCl, let sit 3–5 minutes, rinse with water d. Check if FTO is removed by measuring the resistance
II. Cleaning of FTO Substrates
  a. Ultrasonic cleaning 15 minutes in an aqueous surfactant at ca. 70° C.
  b. Rinse thoroughly with ultrapure water and dry in air
  c. Ultrasonic rinsing with ultrapure water 15 min at ca. 70° C.
  d. Ultrasonic cleaning 15 minutes in pure isopropanol at ca. 70° C.
  e. Blow dry with nitrogen
III. Preparation of Blocking Layer
  a. Put substrate with a mask onto hotplate, heat to 45° C.
  b. Using an atomiser, make several passes spraying 0,2 M titanium acetylacetonate in ethanol onto the substrate. Let sit 1 minute between passes (3 seconds per pass, sprayer distance 20 cm, 4 passes)
  c. Temper film at 500° C. in air for one hour.
IV. Preparation of Nanoporous $TiO_2$ Layer
  a. Screen printing: use a $TiO_2$ paste with a screen structured with the desired geometry (thickness depends on screen mesh); resulting standard thickness is about 3 μm; doctor blading is an alternative technique to make porous $TiO_2$ layer
  b. Sintering of film
    1. Heat the substrates up to 85° C. for 30 minutes to dry the film
    2. Sinter at 450° C. for ½ hour, ideally under oxygen flow, otherwise in air
    3. Let sample cool down slowly to avoid cracking
V. Dyeing of Nanocrystalline $TiO_2$ Film
  a. Prepare a solution of Ru-the dye in ethanol, concentration ca. $5 \times 10^{-4}$ M
  b. Put the ca. 200° C. warm substrates into the dye solution.
  c. Let them sit in the dye-solution at room temperature in the dark for about 8 hours or overnight.
  d. Remove from dye solution, rinse with ethanol and let dry several hours or overnight in the dark.
VI. Deposition of Hole Conductor
  a. Prepare a solution of hole conductor. Current "standard conditions" are:
    Solvent: chlorobenzene (plus ca. 10% acetonitrile from dopant solution)
    Hole conductor: concentration (5–60 mg/substrate)
    Dopant: tribromophenylammonium hexachloroantimonate (ca. 0,2 mol % of hole conductor concentration, to be added from a solution in acetonitrile)
    Salt: $Li((CF_3SO_2)_2N)$, (ca. 9 mol %)
  b. Spin-coat the solution onto the film using the following parameters
    1. Time before spinning: ca. 30 sec.
    2. Spinning speed: 1000 rpm
    3. Spinning time: 30 sec.
    Or pipetting: evaporate the hole conductor by placing the solution on top of the porous layer, heat the substrates up to 50° C. to become rid of the solvent and to melt the hole conductor into the pores.
  c. Let the samples dry at least several hours in air or preferably overnight.
VII. Deposition of Counterelectrode
  a. Evaporate the counterelectrode (currently gold)
  b. Thickness: ca. 30–50 nm The invention is further illustrated by the following figures and examples from which further embodiments and advantages may be taken and where FIG. 1 shows the synthesis scheme of organic hole transporting agents, FIG. 2 shows the thermal data of compositions comprising MEH-TDAB and MH-TDAB, more particularly the variation of Tg, Tm ($2^{nd}$ heat run) and Tcr ($1^{st}$ cool run) and the melt and recrystallization enthalpies of the various mixtures of MEH-TDAB and MH-TDAB, FIG. 3 shows DSC heating and cooling curves for the 60:40 (wt %) mixture of MEH-TDAB and MH-TDAB, FIG. 4 shows the X-ray powder diffraction pattern of the 60:40 (wt %) mixture of MEH-TDAB and MH-TDAB, FIG. 5 shows the basic design of the inventive solar cell, FIG. 6 shows current-voltage characteristics of solar cells prepared according to example 3, FIG. 7 shows the variation of the photocurrent with regard the radiation wavelength, FIG. 8 shows an SEM image of the $TiO_2$ particles unable as semiconductor material, FIG. 9 shows the I/V curve of the first type of solar cell as prepared in example 4, FIG. 10 shows the I/V curve of the fourth type of solar cell as prepared in example 4, FIG. 11 shows some possible TPD derivatives and their DSC (expressed with a coolong and heating rate of 10 K/min, and FIG. 12 shows some possible TDAB derivatives including their Tg, Tcr (i.e. crystallisation temperature) and HOMO,

EXAMPLES

Example 1
Synthesis of New Hole Transporting Agents

In order to develop HTM systems with low oxidation potentials, low melt viscosity and stable amorphous nature, both strategies of developing new compounds as well as composites were followed. The development of branched or starburst compounds with suitable soft alkyloxy chains (to decrease the viscosity and increase the capillary effect) was undertaken. Some novel starburst compounds, tris (diarylamino)benzenes (TDABs) were synthesized as per scheme shown in FIG. 1 The hexaanisyl derivative (Han-TDAB) is a symmetrically substituted compound, whereas the other two derivatives, tris(methoxyphenyl ethylhexyoxy phenyl amino) benzene [MEH-TDAB] and tris (methoxyphenyl hexyloxy phenyl amino) benzene [MH-TDAB] are unsymmetrically substituted. Due to the flexible alkyl groups, the latter are expected to have low melting and glass transition temperatures. The purification was achieved by column chromatography. (The synthesis scheme is also disclosed in Gauthier, S.; Frechet, J. M; Synthesis 1987, 383)

Example 2
Characterization of the Hole Transporting Agents of Example 1 and Mixtures thereof
1. Thermal and Electrochemical Properties The thermal properties were examined using differential scanning calorimetry (DSC) and the electrochemical properties were studied using cyclic voltammetry (CV).

Cyclic voltammetry measurements (CV) were carried at a glassy carbon electrode in a solution of acetonitrile or tetrahydrofurane containing 0.1 M tetrabutylammonium hexafluorophosphate (TBAPF6) using a three electrode cell and potentiostat assembly from EG&G Princeton Applied Research.

The potentials were measured against $Ag/AgNO_3$ as reference electrode. Each measurement was calibrated with the internal standard, ferrocene/ferrocenium (Fc) redox system. The HOMO (highest occupied molecule orbital) and LUMO (lowest unoccupied molecule orbital) values of the materials were determined from oxidation and reduction potentials, respectively, by taking the value of −4,8 eV as HOMO energy level for the Fc standard system with respect to zero vacuum level as described by Daub et al. Adv. Mater. 1995, 7, 551. This value is obtained by approximation from the calculated value of −4,6 eV for standard electrode potential (E°) for normal hydrogen electrode NHE on the zero vacuum level and the value of 0.2 V for Fc vs. NHE neglecting the solvent effects. The CV data for the compounds HAn-TDAB, MEH-TDAB and MH-TDAB are tabulated in table 1.

TABLE 1

Cyclic voltammetry data and HOMO energy values of HAn-TDAB, MEH-TDAB and MH-TDAB.

| Compounds | $E_{OX1}$ vs. Ag/AgNO$_3$ [V] | $E_{Fc}$ vs. Ag/AgNO$_3$ [V] | $E_{OX1}$ vs. Fc [V] | HOMO [eV] |
|---|---|---|---|---|
| HAn-TDAB | 0.23 | 0.05 | 0.18 | −4.98 |
| MEH-TDAB | 0.25 | 0 06 | 0.19 | −4.99 |
| MH-TDAB | 0.23 | 0.05 | 0.18 | −4.98 |

As expected, the compounds show the same oxidation potential for the first oxidation which is also reversible. It means that the compounds behave electronically in a similar manner although they differ in their thermal properties and amorphous nature. This allows to make composites of these materials of any composition without varying the oxidation potential.

Therefore, mixtures of MEH-TDAB with varying amounts of MH-TDAB were prepared and the thermal properties were studied using differential scanning calorimetry (DSC).

2. DSC Measurements and Phase Diagram of Hole Transporting Material Mixtures

Various mixtures of the composite as described in example 2 comprising of MEH-TDAB and MH-TDAB were prepared by deep freezing the mixtures and the thermal properties were examined using DSC. The thermal data is plotted in FIG. 2.

As can be taken from FIG. 2 the mixture with 60% of MEH-TDAB exhibit the lowest melting point of 30° C. and there is no recrystallization effect for this composition. This composite has also the lowest Tg value of −1.2° C. On comparing the melt enthalpies for first heating and second heating runs, mixtures with 60–80% of MEH-TDAB have negligible melt enthalpy in the second heat run. These mixtures also do not crystallize on cooling from melt or heating above Tg. The mixture with 80% of MEH-TDAB and 20% of MH-TDAB has Tg value of −1.4° C. and a Tm of 107,4° C. (2$^{nd}$ heat run) and does not show any recrystallization.

3. DSC Heating and Cooling Curves as Well as Powder X-ray Diffraction for the 60:40 (wt %) Mixture of tris (methoxyphenyl ethylhexyloxy phenyl amino benzene [MEH-TDAB] and tris(methoxyphenyl hexyloxy phenyl amino) benzene [MH-TDAB]

Further characterization of the 60:40 (wt %) mixture of tris(methoxyphenyl ethylhexyloxy phenyl amino benzene [MEH-TDAB] and tris(methoxyphenyl hexyloxy phenyl amino) benzene [MH-TDAB] using DSC and X-ray diffraction was done.

The DSC measurements for repeated cycles of heating and cooling as shown in FIG. 3 clearly indicates that the crystalline nature of the mixture is almost neglible. The mixture shows a Tg at 7° C. and a very small melting peak around 36° C. The DSC heating was performed at 10 K/min.

The X-ray diffraction of a sample of the 60:40 mixture in capillary at room temperature exhibits almost a broad pattern characteristics for amorphous material as can be taken from FIG. 4. A very small sharp signal for crystalline part is seen at low degrees.

Example 3

Preparation of Solar Cells

A series of hybrid solar cells having the structure, FTO/ TiO$_2$ compact layer (30 nm)/TiO$_2$ nanoporous layer (3 μm)/Ru 535-TBA/SpiroHTM{OMeTAD doped withN (PhBr)$_3$SbCl$_6$ and Li[(CF$_3$SO$_2$)$_2$N]} were prepared. The basic design of such a solar cell is shown in FIG. 5. The composition of the HTM, i.e. the hole transporting material or agent, dopant and salt are in the same proporation as given in the literature (U. Bach et al., Nature, 395, 583, 1998).

The current-voltage characteristics of all the cells were measured which is shown in FIG. 6. In FIG. 7, the variation of the photocurrent with respect to the radiation wavelength for these cells is given. The incident photon to current conversation efficiency, IPCE in the visible region (400–550 nm) is about 10%. The cells s266, s267 and s268 represent cells prepared on three similar FTO substrates and the last additional number represent the four individual cells on each substrate, all prepared under the same conditions.

Example 4

Preparation of Solar Cells Comprising 60:40 Mixture of MEH-TDAB and MH-TDAB

The 60:40 composite material comprising MEH-TDAB and MH-TDAB was used to make solar cells similar to the preparation described in example 3. However, the spiro hole conductor was replaced by a mixture of 60:40 (weight %) comprising MEH-DAB and MH-TDAB. The series of solar cells were prepared in two different ways, either by spin-coating or pipetting the hole conductor. The respective results are shown in table 2.

TABLE 2

Characterisation of a 60:40 mixture of MEH-TDAB and MH-TDAB.

| material | technique | Voc [mV] | Isc [μA/cm$^2$] | FF [%] | η [%] |
|---|---|---|---|---|---|
| 5 mg/substr. 60:40 | pipetting from cyclohexanone | 245 | 70 | 29.2 | 0.005 |
| | pipetting from chlorobenzene | 331 | 17 | 29 | 0.002 |
| 5 mg/substr. spiro | | 440 | 37.3 | 34.6 | 0.006 |
| 15 mg/substr. 60:40 | spincoating from chlorobenzene | 454 | 197 | 28 | 0.014 |
| 30 mg/substr. 60:40 | | 577 | 130 | 32.8 | 0.02 |

For further characterisation of these solar cells it is referred to the corresponding I/V curves of the first and fourth of the above given solar cells.

The features of the present invention disclosed in the specification, the claims and/or the drawings may both separately and in any combination thereof be material for realizing the invention in various forms thereof.

What is claimed is:

1. A compound utilized as a hole transporting agent which is a tris (aryl methoxyphenyl amino) benzene derivative represented by formula (I):

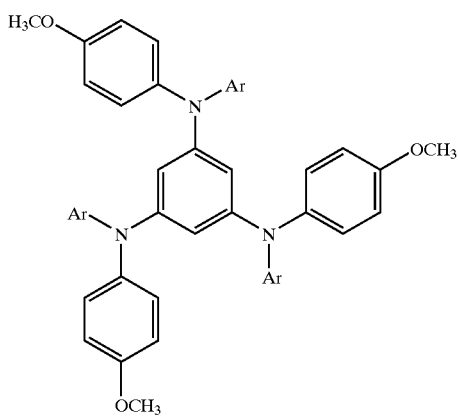

(I)

wherein Ar is a substituent represented by formula (II):

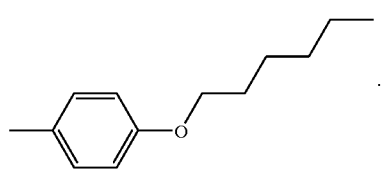

(II)

2. A photoelectric conversion device, comprising the compound according to claim 1.

3. A mixture comprising a first compound according to claim 1 and a second compound which is a tris (aryl methoxyphenyl amino) benzene derivative represented by formula (III):

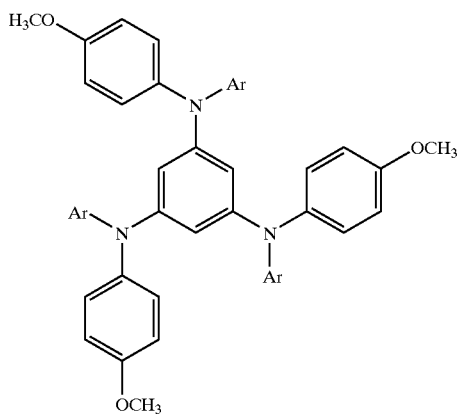

(III)

wherein Ar is a substituent represented by formula (IV):

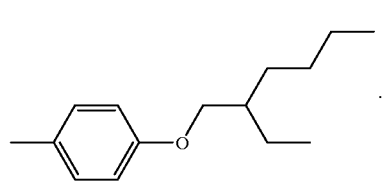

(IV)

4. A method for the production of a photoelectric conversion device, comprising the step of applying the mixture according to claim 3 to a semiconductor.

5. The method for the production of a photoelectric conversion device according to claim 4, wherein the semiconductor is sentisized with a dye.

6. The mixture according to claim 3, wherein the ratio in said mixture of the first compound in relation to the second compound is from about 60:40 to about 20:80, and wherein the amount of each compound is expressed as wt.-% of the total weight of the mixture.

7. The mixture according to claim 6, wherein said ratio is 40:60.

8. A photoelectric conversion device, comprising the mixture according to claim 6.

9. A method for the manufacture of a photoelectric conversion device, comprising the step of applying the mixture according to claim 6 to a semiconductor.

10. A method for the production of a photoelectric conversion device comprising an organic electrically conducting agent having a melting temperature and a glass transition temperature, comprising the step of applying the compound according to claim 1 as said organic electrically conducting agent to a semiconductor.

11. The method for the production of a photoelectric conversion device according to claim 10, wherein the semiconductor is sensitized with a dye.

12. The method according to claim 10, wherein the application step is carried out at a temperature at or above the glass-transition temperature of the electrically conducting agent.

13. The method according to claim 10, wherein the method further comprises at least one of the following steps:

providing a semiconductor;

melting the organic electrically conducting agent;

applying said organic electrically conducting agent to said semiconductor sensitized with a dye; and connecting electrodes to said semiconductor and to said organic electrically conducting agent.

14. The method according to claim 10, wherein said organic electrically conducting agent is applied to said semiconductor such that a layer of said agent persists on top of said semiconductor.

15. The method according to claim 10, wherein said method comprises the step of cooling the semiconductor and said organic electrically conducting agent to a temperature below said melting temperature and above the glass transition temperature of said organic electrically conducting agent.

16. A compound utilized as a hole transporting agent which is a tris (aryl methoxyphenyl amino) benzene derivative represented by formula (III):

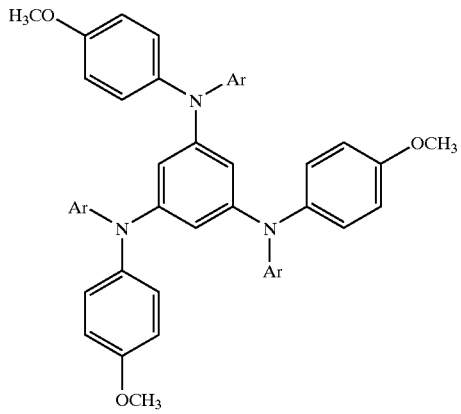

wherein Ar is a substituent represented by formula (IV):

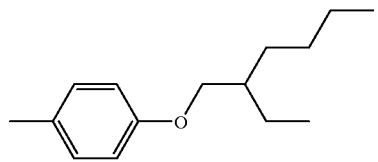

17. A photoelectric conversion device, comprising the compound according to claim 16.

18. A method for the production of a photoelectric conversion device, comprising the step of applying the compound according to claim 16 to a semiconductor.

19. The method for the production of a photoelectric conversion device according to claim 18, wherein the semiconductor is sensitized with a dye.

* * * * *